United States Patent
Black et al.

(10) Patent No.: US 8,342,735 B2
(45) Date of Patent: Jan. 1, 2013

(54) REACTOR COMPRISING AN ANNULAR REACTION SPACE

(75) Inventors: Richard A. Black, Wirral (GB);
Stephen John Curran, York (GB);
James Blackhurst, Wirral (GB)

(73) Assignee: University of Strathclyde, Glasgow (GB)

( * ) Notice: Subject to any disclaimer, the term of this patent is extended or adjusted under 35 U.S.C. 154(b) by 1018 days.

(21) Appl. No.: 12/088,892

(22) PCT Filed: Oct. 2, 2006

(86) PCT No.: PCT/GB2006/003671
§ 371 (c)(1),
(2), (4) Date: Sep. 18, 2008

(87) PCT Pub. No.: WO2007/039726
PCT Pub. Date: Apr. 12, 2007

(65) Prior Publication Data
US 2009/0053811 A1     Feb. 26, 2009

(30) Foreign Application Priority Data
Oct. 1, 2005   (GB) .................................. 0520021.7

(51) Int. Cl.
*B28C 1/16*   (2006.01)
(52) U.S. Cl. ........................................................ 366/78
(58) Field of Classification Search ............... 366/78
See application file for complete search history.

(56) References Cited

U.S. PATENT DOCUMENTS

| | | | |
|---|---|---|---|
| 4,175,871 | A | 11/1979 | Suh et al. |
| 2002/0106625 | A1 | 8/2002 | Hung et al. |
| 2004/0058434 | A1 | 3/2004 | Gault |
| 2005/0095711 | A1 | 5/2005 | More |

FOREIGN PATENT DOCUMENTS

| | | |
|---|---|---|
| DE | 42 07 819 | 9/1993 |
| EP | 1 504 809 | 2/2005 |
| GB | 2097817 | * 3/1982 |
| JP | 10 327842 | 12/1998 |
| WO | WO 03/093408 | 11/2003 |

OTHER PUBLICATIONS

J.M. Skotheim, L. Mahadevan; *Soft Lubrication: The Elastophdrodynamics of Nonconforming and Conforming Contacts*; American Institute of Physics; Published online Sep. 2, 2005.
Examination Report for European Patent Application No. 06 794 623.6, dated May 25, 2010.
Hammond, T.G., et al.; "Optimized suspension culture: the rotating-wall vessel"; American Journal of Physiology Renal Physiology; vol. 281; Issue 1; 2001; pp. F12-F25.
International Search Report for PCT Application PCT/GB2006/003671; Filed Oct. 2, 2006; Date of Completion Dece4mber 14, 2006; Date of Mailing Jan. 1, 2007.
Written Opinion for PCT Application PCT/GB2006/003671; Filed Oct. 2, 2006; Date of Completion Dece4mber 14, 2006; Date of Mailing Jan. 1, 2007.

* cited by examiner

*Primary Examiner* — Maryam Monshipouri
(74) *Attorney, Agent, or Firm* — Alston & Bird LLP

(57) ABSTRACT

A biological or chemical reactor (2) has an inner vessel (4) disposed within an outer vessel (6) and an annular space (16) defined therebetween in which fluid is to be contained. The fluid comprises reactants of a biological or chemical reaction. A reaction support (10a) is disposed in an opening in a wall of one of the vessels and is designed to support a structure such as a scaffold that receives fluid under pressure from the annular space. The reactor generates hydrodynamic pressure and shear stress in the fluid within the annular space, upon relative rotational movement between the vessels so as to drive the fluid through intersticies in the scaffold.

76 Claims, 8 Drawing Sheets

REACTOR COMPRISING AN ANNULAR REACTION SPACE

This application is a 371 of PCT/GB06/03671 filed Oct. 2, 2006, which claims priority to United Kingdom application 0520021.7 filed Oct. 1, 2005.

The present invention relates to reactors, and particularly to reactors for carrying out biological or chemical reactions. The invention extends to methods of carrying out biological or chemical reactions in the said reactor, and in particular to methods of growing bone and/or articular cartilage in vitro.

Many of the procedures used to treat patients with osteoarthritis and age-related deterioration of the synovial joints do not work indefinitely, and up to one third of interventions fail, most often as a result of infection, aseptic loosening and osteolysis. The ramifications of such a high failure rate are considerable, both to patient and health-care provider, given the number of revision procedures that must be performed each year by orthopaedic surgeons throughout the world. It is clear that the quality of life of a substantial number of these patients would undoubtedly be improved and healthcare costs lowered if the long-term success of joint replacement surgery were to increase. Therefore, there is a pressing need to provide technology that can be exploited by orthopaedic surgeons and device manufacturers to improve the success of cell-based therapies used to treat patients with bone and joint disease.

There is increasing evidence that the quality of cartilage constructs grown in vitro depends on the conditions under which these are grown in culture. A range of different tissue engineering bioreactor is in use worldwide, both in research labs and commercially. For example, spinner flask cultures or impeller stirred reactors are commonplace. However, the fluid flow field that exists in a magnetic spinner flask or impeller stirred bioreactor is far from uniform, and as a result are not well-suited for culturing mammalian cells and engineered tissues. Ideally, a well-defined, scaleable hydrodynamic environment is required for Tissue Engineering applications, where the object is to produce fully-functional tissues in vitro that may be used to restore, enhance or replace those natural tissues of the human body that may become damaged through disease or injury, for example cartilage tissue.

Rotating wall vessel (RWV) bioreactors have been proposed as a means of controlling the fluid dynamic environment during long-term culture of mammalian cells and engineered tissues. An RWV bioreactor includes a pair of concentric cylinders with media and cells (or cell-seeded constructs) occupying the annular space (annulus) in between the two cylinders. They are normally configured such that the outer wall rotates, thereby generating a laminar Couette flow in the annulus. In addition, RWVs may also be configured to generate Taylor vortex flows, where inner cylinder rotation provides a simple yet effective means of generating diverse, reproducible and scalable flow states within rotating wall vessels. Since the flow regime in a so-called Couette-Taylor bioreactor may be accurately predicted and controlled, so, too, can forced convective transport.

RWVs generally take two forms. High Aspect Ratio Vessels (HARV) and Slow Lateral Turning Vessels (SLTV), with oxygenation via a gas-permeable membrane on the inner cylinder. In contrast to conventional impeller stirred bioreactors, where excessive shear forces due to fluid motion on the one hand, and an insufficient supply of oxygen on the other, contribute to loss of cell viability, RWVs provide a relatively low shear environment. When operated on a horizontal axis, conditions approaching microgravity may be achieved that favour more uniform tissue formation, resulting in cartilaginous tissue having biochemical and biomechanical properties that are superior to those grown under static conditions or in stirred-flask bioreactors, and which have mechanical properties approaching that of native cartilage.

Rotating wall vessels have been utilised to culture osteoblast-like cells, both in free suspension and on microcarriers, and chondrocytes. In the latter system, porous 3D scaffolds were mounted on the surface of the inner cylinder where they were seeded with bovine chondrocytes to become what are commonly referred to as "constructs" and subjected to shear stress alone as the outer cylinder is rotated at constant speed. However, a problem with RWV bioreactors is that while such flow conditions provide a well-defined flow field and low shear stress environment in which cells can grow, mass transport is often a limiting factor, especially in larger systems.

A further problem with existing RWV reactors is that the pressure in the annular space between the two cylinders has to be applied from an external source. Pressurization of fluid in the annular space of the reactor is achieved either pneumatically or hydraulically. Hence, such externally applied pressure is, by definition, hydrostatic, i.e. the pressure of the fluid is constant throughout the annular space. It will be appreciated that when the annular space, and hence the fluid therein, are under hydrostatic pressure, there are no pressure gradients within the fluid within the space, and the pressures exerted on the fluid in the annular space of known reactors are therefore substantially equal in all directions.

As a result of the hydrostatic pressure created in the annular space of existing reactors, it is not possible to set up conditions, which are directly comparable to the conditions found in diarthroid synovial joints growing in vivo. Hence, tissues grown in vitro in existing RWV bioreactors tend to be inferior.

Furthermore, in a conventional RWV reactor, the relative rotational movement between the rotating vessels results in the generation of velocity gradients within the fluid contained therebetween, the magnitude of which depends on the relative motion of the vessels and the distance therebetween. The shear stresses generated within the fluid, in turn, are a function of the viscosity of the medium contained therein.

Another problem with existing RWV reactors is that it is very difficult, if not impossible, to achieve interstial flow within constructs grown therein. Any displacement of fluid in the construct is secondary to shear-induced deformation of the construct.

It is therefore an object of the present invention to obviate or mitigate one or more of the problems of the prior art, whether identified herein or elsewhere, and to provide an improved reactor in which reactions of a chemical and/or biochemical nature may be carried out.

The inventors focussed their research on the use of RWV reactors, in order to see if they could be designed to improve the efficiency of chemical or biological reactions carried out therein. To their surprise, the inventors found that it is possible to modify the design of RWV reactors so that a biological or chemical reaction carried out therein could be dramatically improved in terms of efficiency, and in terms of improving the conditions created within the rotating vessels of the reactor.

Hence, according to a first aspect of the present invention, there is provided a reactor comprising an inner vessel disposed within an outer vessel, which vessels define a substantially annular space therebetween in which fluid is contained, which fluid comprises reactants of a biological or chemical reaction, wherein the reactor is adapted in use to generate hydrodynamic pressure and shear stress in the fluid within the annular space, upon relative rotational movement between the vessels.

Hence, in contrast to known reactors, in the reactor according to the first aspect of the invention, the relative rotational movement between the inner and outer vessels results in the generation of hydrodynamic pressure within the annular space in addition to fluid shear stress.

By the term "hydrodynamic pressure", we mean the pressure of the fluid comprising the reactants is not the same throughout the annular space, because it changes over time due to the relative rotational movement of the fluid contained between the inner and outer vessels.

By the term "shear stress", we mean the drag force per unit area that is exerted on one surface by the other by virtue of the viscosity and velocity gradient of the fluid medium therebetween.

By the term "relative rotational movement between the vessels", we mean that either the inner and/or the outer vessel rotates in either direction, and at any speed. Hence, the reactor according to the invention is preferably adapted to automatically generate its own pressurization in the annular space, thereby obviating the requirement for an external pressurization source, or augmenting that which may be applied externally. Furthermore, hydrodynamic pressure so generated is particularly advantageous as it causes cyclic deformation and fluid shear flow in the fluid within in the annular space by virtue of the relative motion between the vessels, and the pressure gradients that develop in the annular space as a result. It will be appreciated that such fluid dynamics can be particularly advantageous for numerous biological and/or chemical reactions, which are not obtainable by using prior art reactors.

Preferably, the outer vessel is substantially hollow, so that the inner vessel may be disposed therein. In addition, the inner vessel may be substantially hollow. Preferably, the outer vessel comprises an inner surface, and the inner vessel comprises an outer surface. The inner surface of the outer vessel preferably opposes the outer surface of the inner vessel thereby defining the annular space therebetween. Hence, it will be appreciated that the annular space is preferably defined by the region between the outer surface of the inner vessel and the inner surface of the outer vessel. Preferably, the annular space is a substantially ring-shaped volume of space between the inner and outer vessels. Preferably, the annular space is adapted to receive the fluid, which fluid may comprise, contain or support reactants of a biological or chemical reaction. Hence, it will be appreciated that the fluid may be the reactant(s) of the reaction, and/or act as a supporting medium for the reactants.

It will be appreciated that the radial distance between the inner surface of the outer vessel and the outer surface of the inner vessel is not constant about the circumference of the vessels. Preferably, the annular space is substantially non-uniform, and preferably, comprises a non-uniform circumferential profile.

Preferably, the reactor is adapted in use to vary the distance between a point on the outer surface of the inner vessel or on the inner surface of the outer vessel and a radially opposing point on the other of said surfaces, upon relative rotational movement between the vessels. Preferably, the distance between the points on the respective surfaces is adapted to vary with respect to time, preferably in a cyclic or reciprocating manner. It will be appreciated that the variation in distance between the opposing points on the two vessels with respect to time, may depend on the profiles of the vessel surfaces, and the speed and direction of rotation. Hence, for example, the variation in distance with respect to time may be linear, non-linear, stepped, or sinusoidal etc.

The inventors have surprisingly found that by varying the distance between the opposing surfaces of the vessels during respective rotation, a so-called "fluid wedge" or "pinch point" is produced, wherein the opposing surfaces come close to each other, thereby pinching or squeezing the fluid (and hence, reactants therein) present within the annular space whilst being subjected to shear as a consequence of being entrained on the opposing surfaces as they move relative to one another. The fluid is thus effectively drawn into the wedge. This action produces pressure gradients in the fluid at or adjacent the pinch point, which gradients cause the hydrodynamic pressure and fluid shear to be generated in the annular space in accordance with the first aspect. Furthermore, interstitial flow may be generated as a consequence. It will be appreciated that in prior art reactors, the distance between the opposing vessel walls always remains constant during rotation thereof, and so a pinch point is never formed. Therefore, the fluid and hence, reactants therein, are not squeezed in the prior art reactors, no pressure gradients are produced, and accordingly, hydrodynamic pressure cannot be produced (i.e. it is hydrostatic).

The inner vessel may be adapted to rotate about an axis. In addition, the outer vessel may be adapted to rotate about an axis. However, preferably the inner vessel and the outer vessel are both adapted to rotate about their respective axes, preferably, independently of each other. The axes may be the same or different. If both vessels rotate, they are preferably adapted to rotate in either direction. Hence, rotation may be either in the same direction or opposite direction. Hence, preferably, at least one of the two reactors is adapted to rotate or move with respect to the other. Furthermore, the vessels may be adapted to rotate in the same direction as each other, preferably at different speeds such that at least one vessel is rotating or moving with respect to the other. Hence, it will be appreciated that the reactor is preferably adapted to operate in the following modes: uni-directional rotation of the vessels; counter-directional rotation of the vessels; at various speeds; accelerations; and frequencies of rotation (i.e. steady state rotation, or dynamic rotation; oscillation, intermittent motion). The relative rotation of the vessels may be restricted to an angle of less than 360° e.g. less than 90° and then the movement reversed so that the pinch point repeatedly passes over the same region.

In one embodiment of the reactor according to the invention, the inner and outer vessels may be concentrically mounted to rotate about the same axis of rotation. This embodiment is illustrated in FIGS. 3 and 4. By the term "concentrically mounted", we mean the vessels have the same centre, which forms the axis about which the vessels may rotate. In this embodiment, it is preferred that the distance between a point on the outer surface of the inner vessel or on the inner surface of the outer vessel and a radially opposing point on the other of said surfaces is non-uniform (not constant) around the annular space during respective rotational movement between the two vessels. The effect of the non-uniform annular space is that the relative rotational movement of the vessels produces the "pinch point" or "fluid wedge" and squeeze-film conditions conducive to hydrodynamic lubrication.

It will be understood that in this arrangement the surfaces of the vessels bounding the annular space do not come into contact, even at the pinch point, by virtue of the hydrodynamic lubrication effect provided by the fluid.

However, in certain embodiments it may be desirable that the surfaces do "interfere" such interference being one way in which a desirable load may be applied to the pinch point. This may be achieved, for example, through the application of torque to one or other vessel, the other vessel being free to rotate and thereby generate and maintain a state of hydrodynamic lubrication that generates a pressure that keeps the surfaces from actual contact.

In one exemplary embodiment, the outer surface of the inner vessel and/or the inner surface of the outer vessel is preferably non-uniform or substantially uneven, for example, due to the presence of raised and/or lowered portions at various positions on the or each surface. It is preferred that the raised or lowered portions are disposed at various positions around the circumference of the vessel. For example, the or each surface may comprise at least one raised portion extending away from the plane of the surface. The, or each, raised portion may comprise a projection, or protrusion. It will be appreciated that this arrangement may be similar to a cam as in an internal combustion engine, except that it, preferably, does not make direct contact with the opposing surface. The, or each, raised portion may be spaced apart, preferably circumferentially, or may be continuous thereby forming at least one ridge, which ridge extends along either the outer surface of the inner vessel and/or the inner surface of the outer vessel. The ridge may extend along the surface in a direction, which is substantially parallel with the rotational axis of the vessel. Alternatively, the ridge may extend in a helical direction around the surface.

Alternatively, or additionally, the or each surface may comprise at least one lowered portion with respect to the plane of the surface. The lowered portion may comprise an indentation or recess. The or each lowered portion may be spaced apart, preferably circumferentially, or may be continuous forming at least one channel, which channel extends along either the outer surface of the inner vessel and/or the inner surface of the outer vessel. The channel may extend along the surface in a direction, which is substantially parallel with the rotational axis of the vessel. Alternatively, the channel may extend in a helical direction around the surface. It will be appreciated that the reactor may comprise any combination of raised and lowered portion(s) on either vessel surface.

For example, as shown in FIG. 3, the outer surface of the inner vessel comprises two raised portions. Preferably, the two raised portions diametrically oppose one another. Hence it is preferred that the distance between a point on the inner surface of the outer vessel and a radially opposing point on the outer surface of the inner vessel is nonuniform (not constant) around the annular space during respective rotational movement between the two vessels. Upon respective rotational movement between the two vessels, the distance between the two points decreases when a raised portion opposes the chosen reference point on the inner surface of the outer vessel. This is the pinch point.

It will be appreciated that in the reactor shown in FIG. 4, the inner surface of the outer vessel comprises two raised portions. Preferably the two raised portions diametrically oppose one another. Hence in this embodiment, it is preferred that the distance between a point on the outer surface of the inner vessel and a radially opposing point on the inner surface of the outer vessel is non-uniform (not constant) around the annular space during respective rotational movement between the two vessels. Thus, upon respective rotational movement between the two vessels, the distance between the two points decreases when a raised portion opposes the chosen reference point on the outer surface of the inner vessel.

In another preferred embodiment of the reactor according to the invention, the inner and outer vessels may be mounted to rotate about different axes of rotation. In this embodiment, it is preferred that the distance between a point on the outer surface of the inner vessel or on the inner surface of the outer vessel and a radially opposing point on the other of the said surfaces is non-uniform, during respective rotational movement between the two vessels. The effect of the non-uniform annular space is that the relative rotational movement of the vessels produces (the "pinch point") conditions favourable for hydrodynamic lubrication. In this embodiment, when the outer vessel is stationary, this is equivalent to the embodiment where the vessels rotate about the same axis (i.e. are mounted concentrically), but where the outer vessel is eccentric and stationary also.

In a preferred embodiment of the reactor according to the invention, the inner and outer vessels may be eccentrically mounted to rotate about the same axis of rotation. This embodiment is illustrated in FIGS. 1 and 2. By the term "eccentrically mounted", we mean the vessels have a different geometric centre/axis, but they have the same rotational axis. In this embodiment, it is preferred that the distance between a point on the outer surface of the inner vessel or on the inner surface of the outer vessel and a radially opposing point on the other of the said surfaces is non-uniform (not constant), during respective rotational movement between the two vessels. It will be appreciated that the magnitude and frequency of hydrodynamic pressure gradients generated within the annular space (and hence fluid therein), and shear flow caused therein, are determined by the speed and direction of rotation, and the degree of eccentricity of the mounting of the vessels about the rotational axis.

In all of the above embodiments, the ends of each vessel may be shaped so as to minimise or eliminate so-called 'end effects' and regions of stasis therein. For example, in the case of cylindrical vessels, each vessel may comprise conically shaped ends.

Preferably, the reactor comprises drive means, which is operable to control the speed, and preferably, the direction of rotation of each vessel. The drive means may comprise at least one motor, which provides sufficient drive to each vessel to cause rotation thereof. Hence, the drive means is preferably adapted to apply torque and thereby drive the rotation of each vessel either in the same direction or in opposite directions, preferably independently, or to apply load. Suitable motors for driving the rotation of the vessels will be known to the skilled technician. However, an example of a suitable motor is a servo-motor.

Preferably, the drive means comprises coupling means, which couples the or each motor to each vessel. The coupling means may comprise a drive belt and/or gearbox. It is preferred that the inner vessel comprises a drive shaft, to which the coupling means may be connected either directly or indirectly. It is preferred that the coupling means is connected either directly or indirectly to the outer vessel. FIG. 6 illustrates a preferred embodiment of the drive means according to the invention.

Preferably, the fluid contained within the annular space comprises or contains the reactants of the biological or chemical reaction. Hence, the fluid may be a support medium for the reactants, and/or may be the reactants themselves. The fluid may be liquid, gaseous, aqueous, and/or organic. The reactants may be solid, gas and/or liquid), and will depend on the nature of the biological or chemical reaction. Hence, it will be appreciated that the reactants may comprise matter in the form of discrete solid, liquid and gas phases (i.e., suspensions, colloids, etc.) and/or gels, or any combination thereof, contained within the annular space. In the case of biological reactions, the reactants may be of a reactive nature, and are preferably biologically/biochemically active. The reactants may, for example, comprise growth media; growth factors; chemotactic factors; cells; and living tissue etc.

Preferably, the reactor comprises fluid feed means adapted in use to feed the fluid to the annular space. The fluid feed means may comprise a conduit through which the fluid may be fed, which conduit may be associated with or extend through the drive shaft. Preferably, the reactor comprises means by which the fluid may be fed into the fluid feed means. It is preferred that such means is provided on the drive shaft and may tale the form of a valve or connector. Examples of a suitable valve or connector include a compression fitting, for example, a Luer lock fitted with a 3-way tap.

Preferably, the inner vessel is adapted to allow fluid to pass therethrough, preferably, from the conduit and into the annular space. For example, a wall of the vessel may be substantially permeable or porous. Hence, advantageously, interstitial flow may be generated as a consequence of the relative rotational movement of the vessels when at least one of the walls is permeable. The reactor preferably comprises pumps, valves, actuators, and/or taps, which are adapted to control flow of the fluid in the reactor.

The reaction may be contained within, or adjacent to, the annular space formed between the inner and outer vessels. It is preferred that the reactor comprises reaction containment means for containing the chemical or biological reaction. Preferably, the reaction containment means is provided on or in a wall of the inner and/or outer vessel. Preferably, the containment means is in fluid communication with the annular space such that the fluid, and hence, reactants may flow therebetween. Preferably, the containment means is in fluid communication with the exterior of the reactor such that reactants may flow therebetween, and preferably, away from the annular space.

The reaction containment means may comprise at least one recess, channel or fenestration provided in or extending through the wall of the inner and/or outer vessel. Preferably, the containment means is provided in the, or each, moving (ie. articulating) vessel. The at least one recess, channel or fenestration may be provided in the outer wall of the inner vessel. However, it is preferred that the at least one recess, channel or fenestration is provided in the inner wall of the outer vessel.

Advantageously, using the reactor according to the invention, it is possible to achieve interstial flow therein, in particular either at or adjacent to the "pinch point", i.e. the position where the distance between the opposing walls of the two vessels come together during respective rotational movement thereof. Hence, it is preferred that the reaction containment means is located at or adjacent the position where the pinch point forms upon relative rotational movement between the two vessels. The interstitial flow urges the fluid in the annular space to be squeezed into and through the reaction containment means, which in turns ensures that reactants of the reaction are fed thereto.

The containment means may comprise a plurality of recesses that are spaced apart along the axis of the vessel. Preferably, the reaction containment means comprises a plurality of spaced apart recesses, which are aligned substantially along the longitudinal axis of the vessel.

The reaction containment means may comprise support means in which the reaction may be carried out. It will be appreciated that the nature of the support means will depend on whether the reaction is chemical or biological, and also the type of reaction being carried out in the reactor. Preferably, the support means is adapted to allow fluid to flow therethrough. For example, the support means may be substantially porous, and may comprise interstices. The support means may provide support for a scaffold structure or simply a porous or microporous membrane.

It is preferred that the support means is mounted such that it is substantially in the same plane as the surface in which is it is fitted, i.e. the surface in which the containment means is provided. It will be appreciated that this is preferably the moving or articulating surface. Advantageously, this minimises bubble formation within the support means, for example, via cavitation. However, in some embodiments, the support means may be substantially raised above, or recessed within, the surface in which it is provided. In such cases, it is preferred that the support means is contoured such that it is hydrodynamic. It will be appreciated that the shape of the contour is designed to optimise the pressure profile across the containment means, and hence support means. However, in use, relative rotational movement between the vessels induces hydrodynamic pressure and fluid shear stress at or adjacent the containment means, and preferably, the support means.

The support means may be placed under load within the containment means in order to contribute to and withstand the build up of hydrodynamic pressure within the annular space upon relative rotational movement between the vessels. For example, the load may be provided by means of an external pneumatic or external hydraulic pressure source. Alternatively, the load may be provided by biasing means, which may be a spring.

The support means may be removeable from the containment means. The support means may be adapted to be slideably removed from the containment means. Preferably, the support means is adapted to be moved in a direction, which is substantially normal (perpendicular) to the surface in which the containment means is provided. In some embodiments, the support means may be adapted to tilt as it is moved in or out of the containment means.

The support means allows the harvesting of any product of the reaction that may be produced under the specific hydrodynamic conditions generated in the annular space. For example, if the reaction is biological, then the support means may be provided to support a tissue of cells, which may grow therein in a suitable scaffold or membrane.

The reactor may comprise one or more membrane(s), which membrane is adapted to control the flow of fluid to and from the reaction containment means. Preferably, the membrane extends across the surfaces of the containment means, and preferably, the support means. Preferably, the membrane is microporous. Advantageously, in use, it is possible to establish differential concentration gradients of various reactants (for example, growth substrates, growth factors, chemotactic factors, etc.) and products of the reaction, across the membrane. Furthermore, it is possible to expose the containment means and preferably the support means to different growth media on either aspect (side) of thereof under the hydrodynamic conditions. It is to be understood that the membrane may be used to perform the job of a scaffold. The porosity of the scaffold and/or membrane may vary across its depth.

Hence, for biological reactions, it will be appreciated that the walls of either the inner or the outer vessels, or both, are adapted to support 3D scaffolds such that the diffusion and convection of tissue culture medium through the interstices of the scaffold and hence, construct is possible. Accordingly, the support means may be slotted into position in the recesses to facilitate introduction and removal of a series of constructs at the same time. It will also be appreciated that the constructs are subjected to fluid shear forces and hydrodynamic pressure across the surface of the construct by virtue of the viscous properties of the culture medium and the fluid flow patterns created within the annular space (i.e. a wide range of laminar and Couette flow regimes within the annular space) as prescribed by the relative motion and separation of the opposing surfaces of the vessels.

For convenience, the containment means may be made of disposable materials. This may also be the case for the vessels themselves, and all tubing, connectors, etc., that make up the system.

It is preferred that the reactor comprises fluid outlet means adapted to remove fluid from the annular space. Hence, preferably, the fluid outlet means is in fluid communication with the annular space, and preferably, the containment means. It may be defined on a wall of a vessel immediately adjacent to the containment means. It will be appreciated that the fluid being removed may comprise unreacted reactants and/or products of the chemical or biological reaction carried out in the reactor. In the case of biological reactions, the removed fluid may comprise growth media, which may contain unused substrates and also products of the reaction.

The reactor may comprise fluid re-circulation means adapted to re-circulate fluid exiting the annular space via the outlet means, and back into the annular space, preferably, via the fluid feed means. The reactor may comprise fluid mixing means adapted to mix the fluid in the outlet means with fluid from the fluid feed means.

Preferably, the reactor comprises securement means adapted to secure the reactor in any spatial orientation, i.e. vertically, horizontally, or any angle therebetween. Hence, the reactor may be operated in a substantially vertical or lateral configuration. The securement means may comprise a manifold, which is adapted to be secured to a support stand.

The reactor may be adapted to rotate the axis of rotation of the vessels, in order to affect, counteract, alter or reverse the effects of gravity. Accordingly, the reactor may itself be mounted about a rotational axis, which axis is independent of the rotational axis of the inner and outer vessels.

The reactor may be contained within a means adapted to monitor and preferably, control the reaction variables within the reactor. For example, such variables may be the pH, temperature, and concentrations of various gases, for example, oxygen, carbon dioxide etc. Said means may comprise an environment chamber, an embodiment of which is illustrated in FIG. 7.

It will be appreciated that the reactor according to the first aspect may be adapted to carry out either a chemical or a biological reaction therein.

Hence, in a second aspect, there is provided a method of carrying out a chemical or biological reaction, the method comprising:—
  (i) feeding fluid comprising reactants of a biological or chemical reaction to the reactor according to the first aspect; and
  (ii) causing relative rotational movement between the vessels in order to generate hydrodynamic pressure and shear stress within the annular space.

Preferably, step (i) of the method comprises feeding the fluid comprising or supporting the reactants into the annular space of the reactor, preferably, via fluid feed means. Preferably, the method comprises removing fluid from the reactor and, preferably the annular space. Preferably, said removing step is via fluid outlet means.

The reaction may be a chemical reaction, in which case the reactor may be referred to as a chemical reactor. The skilled technician will appreciate the various types of chemical reaction, which may be carried out with the method of the second aspect. In particular, suitable chemical reactions will include those in which hydrodynamic pressure and shear stresses applied to the fluid comprising the reactants would be an advantage, for example, polymerisation reactions. Hence, examples of a chemical reaction, which may be carried out with the method of the second aspect in the reactor of the first aspect include various addition polymerisation reactions (i.e. either simple, co-, or hetero-polymerisation) and condensation polymerisation. These reactions may be batch, continuous, or bulk polymerisation reactions, and may be either solution, suspension or emulsion polymerisation and polymer processing reactions.

The inventors believe that any monomer capable of polymerising to form a polymer, or capable of co-polymerising with prepolymers may be used in the method of the second aspect. Hence, the reactor according to the first aspect may facilitate the production of a wide range of polymers and co-polymers.

Hence, preferably, step (i) of the method according to the second aspect comprises feeding fluid comprising suitable monomers and/or pre-polymers into the annular space in the reactor. Step (ii) of the method comprises actuating the reactor such that relative rotational movement occurs between the vessels, whereupon hydrodynamic pressure and shear stress are generated within the annular space. The hydrodynamic pressure and shear stress generated in step (ii) advantageously influence the polymerisation process, and the formation (and alignment) of cross-links between monomer and polymer chains. The specific speed and degree of relative rotational movement between the vessels in step (ii) will depend on the specific reaction being carried out in the reactor.

The skilled technician will also appreciate the various reaction parameters for each chemical reaction, which will need to be controlled, for example, the temperature and pressure to which the reactants may need to be subjected.

For example, in one embodiment, the method according to the second aspect may comprise the polymerisation and subsequent processing (extrusion) of a thermoplastic polyurethane. This reaction may comprise mixing suitable monomers and/or suitable prepolymers in the annular space of the reactor. The skilled technician will appreciate that polyurethanes are formed by reacting a polyol (an alcohol with more than two reactive hydroxyl groups per molecule) with a diisocyanate or polymeric isocyanate, preferably, at an elevated temperature, such as about 40° C.

Hence, the fluid being fed into the annular space in step (i) of the method preferably comprises polyol and preferably, an isocyanate or a polymeric isocyanate.

The polyol may be either a polyester or a polyether. An example of a polyether polyol is polytetramethylene glycol. The isocyante may be a diisocyanate. The polyisocyanate may be selected from a wide range of aliphatic, cycloaliphatic and aromatic polyisocyanates, known to the skilled technician. Examples of suitable aromatic polyisocyanates are methyl-diisocyanate (MDI) and toluene diisocyanate (TDI). The product of the polymerisation reaction is therefore a poly(ether)urethane urea.

The skilled technician will appreciate that many industrial polyurethane foams are made with the aid of at least one catalyst to ensure complete polymerisation and to improve the strength and structure of the resulting material or foam. A typical processing temperature may be about 40° C. The reaction may be conducted in the presence of a suitable catalyst. A suitable catalyst may be an amine-containing compound. The method may comprise grafting the catalyst into the polyol, thereby saving customers a formulating step. Other suitable catalysts, which may be used in the method may include Titanium-based catalysts, which are hydrolytically stable alternatives to amines that allow curing temperatures and times to be tailored to the requirements of a specific application.

However, the method according to the second aspect preferably comprises reacting the monomer or prepolymer with a hydrogen-containing reactant (e.g water), in the absence of a catalyst. For example, when preparing a hydrophilic foam or hydrogel, for use in medical applications (e.g. woundcare, barrier contraceptives, ostomy devices, foams, etc.). Because of the amount of water involved, the energy associated with this exothermic reaction does give rise to a great increase in temperature, with the result that curing may take place at room temperature allowing the incorporation of temperature sensitive components (i.e. proteins, peptides, pharmaceuticals, etc.) into the polymer during curing, compounds that would otherwise be denatured at higher processing temperatures.

Preferably, the reaction is stopped before the polymerisation is complete. Preferably, the method further comprises contacting the reactants in the annular space with a suitable chain extender. Hence, preferably, the fluid being fed into the reactor in step (i) of the method comprises a suitable chain extender.

An example of a preferred chain extender, which may be used in the method, is a diol. Examples of suitable diols include 1,6-hexane diol, 2-ethyl-1,3-hexanediol (EHD), and 1,4-Butanediol. In addition, a glycol may also be added to the reaction. A preferred glycol is a low molecular weight glycol such as 1,4-Butanediol.

In one embodiment, the fluid in the annular space comprises the reactant(s), or incorporates the reactants from which the product (polymer, copolymer) is subsequently extracted. Hence, the polymerisation reaction takes place under the action of hydrodynamic pressure and shear, which are known to influence the polymerisation process, and the formation (and alignment) of cross links between monomer and polymer chains.

In another embodiment, the method may comprise reaction injection moulding (RIM). In this embodiment, the reactants may be mixed in the annular space at relatively low temperatures before being injected into a closed mould. An exothermic reaction occurs, and consequently reaction injection moulding requires far less energy than any other injection moulding system. It is envisaged that the mixing of the reactants would take place in the annular space, and the mould would be the containment means where the polymerisation reaction would complete.

In another embodiment, the method may comprise extrusion of the reaction product. Polymer resins or the products of the polymerisation reaction may be extruded from the reactor through the containment means, which in this case may take on the role of a die. The process of extrusion may be facilitated by the elevated temperatures and pressures generated within the annulus by means of hydrodynamic lubrication. Advantageously, extrusion of the polymer product, co-polymer, composite (where the product incorporates other solid matter, possibly non-reactive, for example, nanoparticulates, fibres, etc., as in fibre-reinforced composites) via the containment means under shear likely to induce alignment of polymer chains, fibres, etc., thereby resulting in directional dependent (anisotropic) mechanical properties (e.g. ultimate tensile strength, modulus of elasticity).

Hence, after the monomer and/or prepolymer have been and a suitable chain extender are reacted in the annular space of the reactor to form the polymer, the polymer product may be extruded under pressure through a die, which may be provided by the reaction containment means, or the reaction support means.

The above methods may be either continuous or batch processes.

Other possible chemical reactions which may be carried out with the method of the second aspect may include gel formation (for example, via coascervation), thermal- and photo-induced cross-linking, and/or on exposure to a catalyst.

Other possible examples of a chemical reaction which may be carried out in the reactor according to the first embodiment, or using the method according to the second embodiment, include the synthesis of nylon, poly(2-hydroxyethyle methacrylate) (PolyHEMA) and poly(lactide). The skilled technician will appreciate which reactants need to be fed into the annular space in the reactor in step (ii) of the method to prepare these compounds, and the required reaction conditions.

Further examples of the processes that could take place in the reactor include the following:

Phase separation. The use of polymers to control the stability/flocculation behaviour of dispersions is common in many industrial processes. Studies have shown that the hydrodynamic conditions that prevail during flocculation determine the properties of the aggregates that form (floc size, structure and strength). The conditions present in the reactor may be conducive to more efficient phase separation and removal of the aggregates that form in the reactor. Here, either or both solid and liquid phases may be considered as 'product'.

Coascervation of natural and synthetic gels and hydrogels (e.g. collagen, elastin, hyaluronan, PEO). These are temperature-dependent processes, where the precursors of the gel cross link when heated to 37° C. There is evidence that the hydrodynamic conditions under which such gelation occurs influences the physical (e.g. turbidity), rheological (e.g. shear-dependent) and mechanical properties of the resulting gels. This effect has been demonstrated with synthetic polymer gels of polyethylene oxide co-polymers (PEO-PLGA-PEO).

It will be appreciated that the above are a selection of examples of suitable chemical reactions that may be carried out in the reactor according to the first aspect using the method of the second aspect.

However, it is preferred that the method according to the second aspect is used to carry out a biological reaction, in which case the reactor of the first aspect may be defined as being a biological reactor, or a bioreactor. For example, a suitable biological reaction, which may be carried out in the reactor includes growing a culture of cells (i.e. in vitro). Hence, the method comprises feeding growth media into the annular space in step (i) of the method. The skilled technician will appreciate the many different types of cell cultures, which may be grown using the method of the second aspect, and also the specific growth conditions (temperature, pressures, media etc) required for growth.

By way of example only, the reactor may be used to grow prokaryotic or eukaryotic cell cultures. Examples of suitable prokaryotes include bacteria, such as *E. coli*, which grow at about 37° C. in a suitable media, such as LB.

Examples of suitable eukaryotes include fungi, such as yeast, which may be grown at about 30° C. in a suitable media, such as YPD. However, preferred examples of eukaryotes, which may be grown in the reactor include mammalian cells.

Hence, it will be appreciated that the reactor according to the first aspect of the invention or the method of the second aspect may be used to grow cells, and preferably, a tissue culture in vitro.

Hence, in a third aspect, there is provided a method of growing a cell culture in vitro, the method comprising culturing cells in the reactor according to the first aspect, and causing relative rotational movement between the vessels in order to generate hydrodynamic pressure and shear stress within the annular space.

Preferably, the method comprises feeding the fluid comprising or supporting reactants of the cell culture into the annular space of the reactor, preferably, via fluid feed means. Preferably, the method comprises removing fluid from the annular space via fluid outlet means.

Preferably, the fluid comprises growth medium in which the cell culture may grow. The fluid may comprise water, and preferably other growth additives required for growth, which will depend on the specific cell culture being grown therein.

For example, the cell culture preferably comprises mammalian cells. Examples of suitable cells, which may be grown in the reactor include chondrocytes (autologous or autogenous); stem cells (e.g. mesenchymal, haematopoeic etc., including embryonic and cloned). Such cell cultures may be grown either in free suspension for example in the annular space. Preferably, the cell culture is grown in the reaction containment means. The culture may be seeded (i.e. supported) on biomaterial substrates, which may be provided in the reaction containment means or the support means. The substrates may be of either synthetic or biological origin.

In a preferred embodiment, the method of the third aspect comprises growing bone and/or articular cartilage in vitro in the reactor of the first aspect.

Hence, in a fourth aspect, there is provided a method of growing bone and/or articular cartilage in vitro, the method comprising culturing bone and/or articular cartilage cells in the reactor according to the first aspect, and causing relative rotational movement between the vessels in order to generate hydrodynamic pressure and shear stress within the annular space.

The degree of hydrodynamic loading and fluid shear stress applied to the bone and/or articular cartilage in the method of the fourth aspect may be adjusted accordingly throughout the period of culture via control of the speed, direction of rotation of and torque applied to the vessels. In addition, control of fluid, media exchange and oxygen tension may also be required. The result of the culture in the reactor of the first aspect using the method of the fourth aspect is that the in vitro conditions provided in the annular space are much more realistic and comparable to the growth environment in vivo for bone and/or cartilage cartilage (e.g. in diarthroid synovial joints), than would be possible by using prior art RWV reactors. As mentioned above, such prior art RWV reactors can only generate hydrostatic pressure. However, the method of the fourth aspect allows for the generation of hydrodynamic pressure and in addition shear stress on the bone and/or articular cartilage cells in the annular space, which creates environmental conditions similar to those generated in viva. Hence, cartilage produced by growing in the reactor according to the first aspect of the invention are much improved to that which is grown using current in vitro culture apparatus and techniques.

The inventors were therefore surprised to find that the method of the fourth aspect allows in vivo growth conditions for cartilage cells to be created. The product of the method (i.e. the cartilage) may then be extracted from the reactor (either the annular space of the reaction containment means if used), and then may be used for implantation in a patient in need thereof.

A preferred method of growing bone and/or articular cartilage in vitro is described in Example 2.

Preferably, the method of the third or fourth aspect comprises culturing bone and/or articular cartilage cells in the annular space, and preferably, the reaction containment means in the wall of either the inner or outer vessel. The containment means is preferably a recess in the vessel wall. The method may comprise loading the reaction containment means with a support means, such as a biomaterial plug or scaffold. Preferably, the surfaces of the support means are modified to promote cell adhesion. Such modification may comprise treatment with plasma, surface treatments and coatings, for example, peptides, proteins either adsorbed or immobilised onto the surface of the scaffold. The bone and/or articular cartilage cells may include osteoblast cells and/or chondrocytes.

Preferably, the method comprises enclosing the reaction containment means with one or more permeable membrane (s). Preferably, the method comprises connecting fluid feed means and preferably, a media reservoir, to the reactor. Preferably, these steps are carried out in a clean room environment, for example, in a laminar flow hood or equivalent thereof.

The method may comprise attaching fluid outlet means to the reactor. Preferably, the method comprises feeding bone-and/or cartilage-forming cells (e.g. mesenchymal stem cells, osteoblasts, and/or chondrocytes) into the reactor via the fluid feed means. This may be by bolus injection into the fluid feed means for example, using a syringe, preferably, via a suitable compression fitting connected to the inlet means. The bone and/or cartilage cells accumulate in and populate the scaffolds and/or membranes under appropriate perfusion conditions.

The reactor may be attached to a chassis or platform, which may then transferred to an environmental control chamber. The media reservoir is preferably filled with culture medium, capped, and vented through a 0.2 μm filter to facilitate sterile gas exchange to the medium. The reactor may then be primed with cell-free culture media by means of a pump. Therefore, in use, the method preferably comprise feeding cell free media into the reactor via the fluid means, and preferably to the annular space.

The method comprises setting up suitable environmental conditions in the chamber so that the reaction may be carried out. Suitable culture conditions will be known to the skilled technician. For example, the reactor and preferably the annular space, is preferably maintained at about 37° C. and about 5% $CO_2$ concentration with appropriate humidity.

It is preferred that the method comprises growing the cell culture under low oxygen concentrations. Suitable oxygen tensions may be between about 1 and 15% (Percent Saturation). The method preferably comprises continuously monitoring various parameters of the reaction, for example, pH, temperature, oxygen concentration, carbon dioxide temperature etc.

The method preferably comprises introducing further bone/cartilage cells via the fluid feed means, which is fed to the annular space. The cells are allowed to perfuse through interstitial spaces in the scaffold, thereby forming a so-called cartilage tissue construct. Once the cells have attached and proliferated within the constructs, media perfusion is applied intermittently as and when nutrients are required, this being determined from pH and oxygen consumption data.

Preferably, the inner and outer cylinders are mounted eccentrically about the same rotational axis. The method comprises rotating the inner and/or outer vessels of the reactor as and when appropriate, also in a prescribed manner, under the power of drive means, e.g. servo motors. As shown in FIG. 2, the eccentricity of the rotation of the two vessels, causes the shape of the annular space to be varied, which in turn imparts radial loading on the cell constructs with a magnitude and frequency that is governed by the speed of rotation and degree of eccentricity of the vessels. The radial loading causes a pinch point to form at the position of the reaction containment means, and hence the support means and therefore cell construct. Hence, the pressure gradients that develop by virtue of the relative motion of the two vessels gives rise to periodic deformation and media flow through the constructs. In use, when a tissue culture is grown in the reactor according to the first aspect, the tissue scaffold preferably adopts the shape of the containment means.

The inventors anticipate that the reactor of the invention improves the uniformity of seeding and the functional properties of three-dimensional cell-seeded scaffolds by culturing them under hydrodynamic conditions that simulate loading conditions found in vivo in normal physiological conditions. This is in contrast to hydrostatic pressure and deformation alone found in prior art reactors. The reactor according to the invention therefore allows the preconditioning of the cartilage or other constructs by means of steady or cyclic, intermittent (variable duty cycle) motion of the inner and outer vessels about their respective axes of rotation.

Finally, the cell constructs may be removed from the reactor, and then used as implants to replace otherwise damaged cells in a patient. Such constructs have been grown in the reactor according to the invention in conditions almost identical to in vivo growth conditions, and therefore act as ideal implants, which are far superior to implants prepared using existing RWV reactors.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which:—

EXAMPLES

Figure 1:
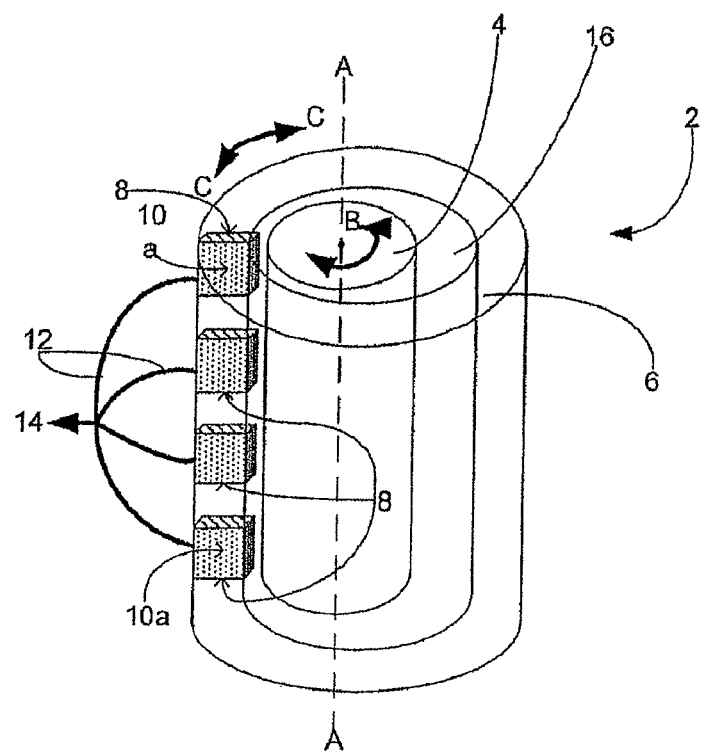
FIG. 1 shows a partially cross-sectional schematic view of a first embodiment of a reactor in accordance with the invention.
Figure 2:
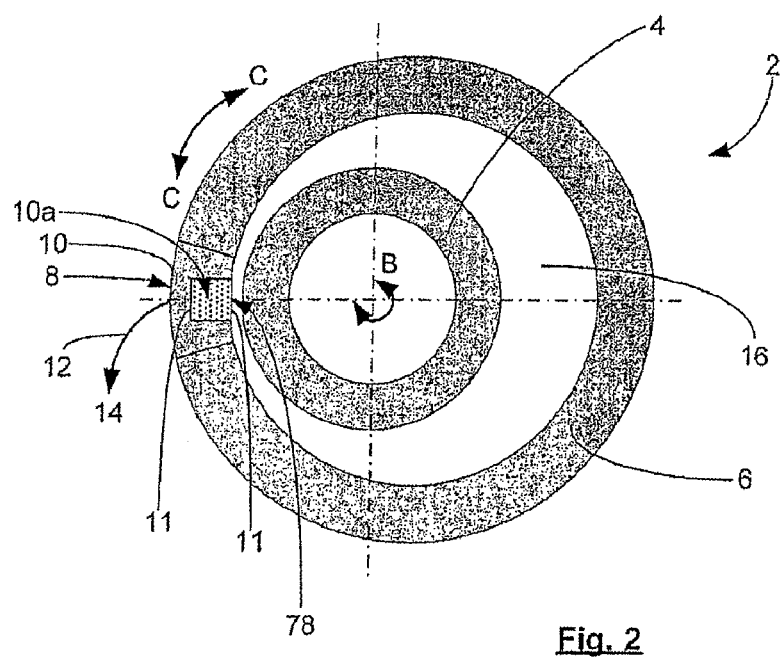
FIG. 2 shows a plan view of the reactor shown in FIG. 1.
Figure 3:
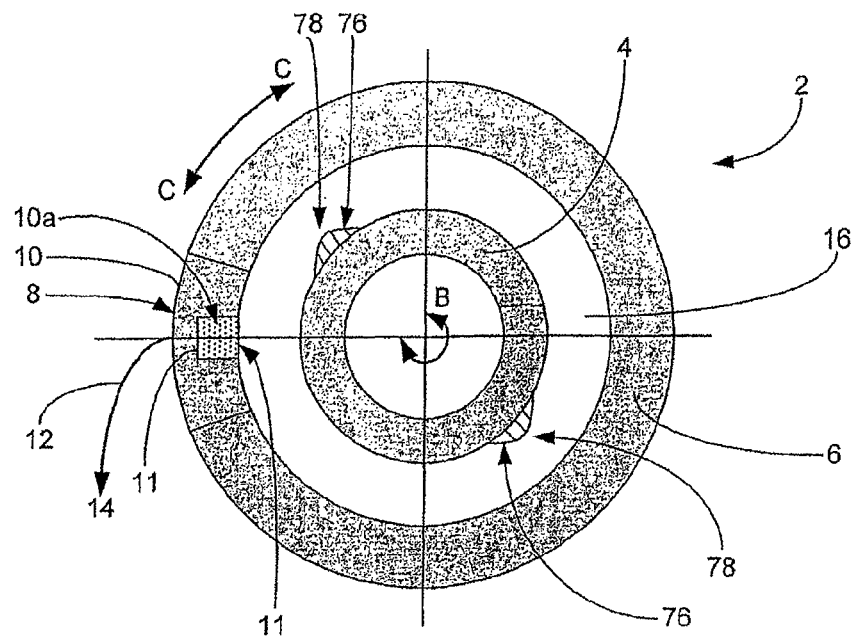
FIG. 3 shows a schematic plan view of a second embodiment of the reactor in accordance with the invention.
Figure 4:
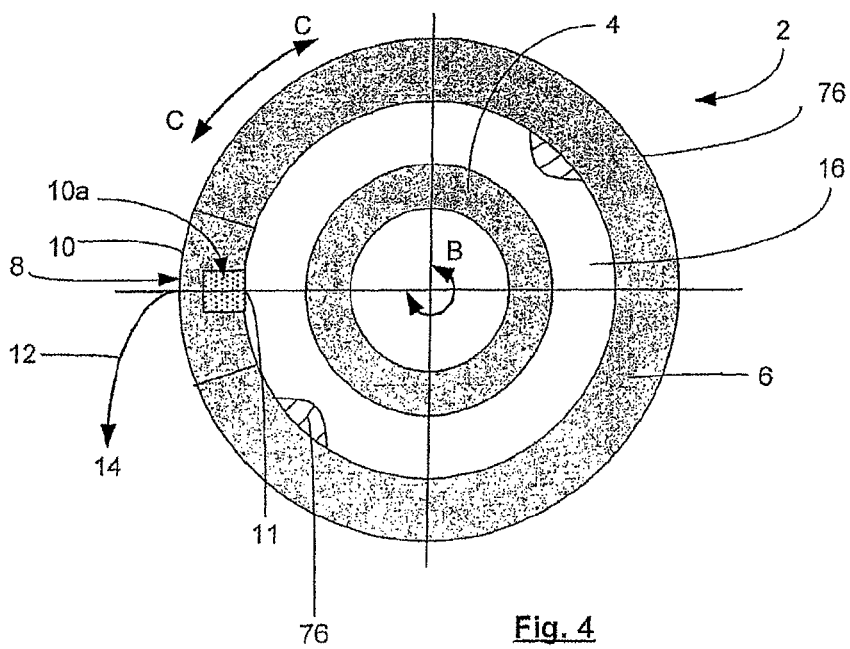
FIG. 4 shows a schematic plan view of a third embodiment of the reactor in accordance with the invention.

The inventors have designed a reactor 2, embodiments of which are shown in the Figures. FIGS. 1 and 2 show a first embodiment of the reactor 2, and FIGS. 3 and 4 illustrate second and third embodiments of the reactor 2, respectively. Other embodiments are shown in FIGS. 10 to 12 and 13. The novel design of the reactor 2, which is able to generate hydrodynamic pressure and shear stresses therein, means that it is perfectly suited for use for carrying out a biological reaction, e.g. for growing a biological culture as described in Example 2, or for carrying out chemical reactions as described in Example 3.

Example 1

The Reactor Design

Referring to FIGS. 1 and 2, there is shown one embodiment of the reactor 2. The components of the reactor 2 are made of 316 L stainless steel such that it may be sterilised by autoclave or SIP (Steam/Sterilisation in Place). The reactor 2 has an inner hollow cylinder 4 and an outer hollow cylinder 6, which together define an annular space (or annulus) 16 therebetween. The annular space 16 is an area of the reactor 2 in which the reactants of a biological or chemical reaction are contained, and which in some embodiments of the invention, the reaction itself may be carried out. The cylinders 4, 6 are circular in cross section, and are mounted on, and rotate about, a common rotational axis defined by line A-A shown in FIG. 1. As illustrated by arrows B and C, each cylinder 4,6 can rotate in either a clockwise or anti-clockwise direction, such rotation being independent of each other. Therefore, for example, the inner cylinder 4 can be arranged to rotate at a certain speed in a clockwise direction, while the outer cylinder 6 is arranged to rotate at a different speed, in an anti-clockwise direction. It should also be appreciated that either the inner or outer cylinder 4,6 could also be kept stationary, while the other cylinder 4,6 is set to rotate in either direction, and or oscillate in through 90°, 180°, or 360°, or any angle in between.

As can be seen more clearly in FIG. 2, the mounting of the two cylinders 4,6 with respect to each other is eccentric, i.e. the two cylinders 4,6 do not have a common centre. Accordingly, as either one or both of the cylinders 4,6 rotate about the same rotational axis A-A, as illustrated by arrows B and C in FIGS. 1 and 2, in either direction, the shape of the annular space 16 between the two cylinders varies in dimension. The eccentric mounting of the two cylinders 4,6 means that the distance between corresponding points on opposing surfaces of the cylinders 4,6 varies over time as they rotate. As shown in FIG. 2, relative rotational movement of the two cylinders 4,6 (i.e. either the inner and/or the outer cylinder rotates in either direction) produces a so-called "pinch point" 78 in the annular space 16. This is a position 78 at which the distance between opposing surfaces of the vessels 4,6 is reduced, and where reactants in the annular space 16 are placed under pressure or 'squeezed'. The eccentric mounting of the two cylinders 4,6 is such that the pinch point 78 is produced at the position of recesses 8, described below. Such squeezing sets up pressure gradients within the annular space 16, which in turn leads to a hydrodynamic pressure system in the space 16. In addition, shear stresses are produced within the annular space 16. As will be described hereinafter, the generation of hydrodynamic pressure and shear stress in the annular space 16 is particularly advantageous when carrying out either biological or chemical reactions in the reactor 2. The relative rotation of the vessels may be restricted to a small angle e.g. less than 90° and the direction reversed so that the pinch point repeatedly passes the recesses 8. Alternatively recesses may be positioned at multiple locations around the vessels so that the pinch point passes over them in turn.

Referring to FIG. 1, the wall of the outer cylinder 6 is provided with a series of multiple spaced apart openings or fenestrations 8, in which a culture of cells may be grown, or in which a chemical reaction may be contained. Each opening is provided with a removeable support plug 10 that effectively closes the opening in the wall. For biological reactions, the plug 10 has a recess facing the annular space 16 that acts as a support for a cell tissue scaffold 10*a*, and for chemical reactions, the plug 10 acts as a support for any suitable structure, as will be described hereinafter. Furthermore, a microporous membrane 11 is provided across the base and/or entrance of each opening 8 and allows reactants (e.g. growth media, or chemical reactants) to pass therethrough, to and from the cells or the chemical reaction, in the scaffold 10*a* that is housed in the support plug 10 in the opening 8. Each opening 8 is also provided with a fluid outlet conduit 12, which feeds chemical reactants or products or growth media to a media storage. Thus the fluid passes from the annular space 16 into the intersticies in the scaffold 10*a*, through the membrane 11 at the base of the support plug 10, through passages in the plug itself (not shown) and out through the outlet conduit 12 to the media storage.

It is to be appreciated that the support plug 10 may take any convenient form that allows it to be removed from the wall of the vessel in which it is received so as to provide access to the scaffold 10*a*. In the embodiment shown in FIGS. 1 and 2 it will be understood that the support plug 10 may be removed from the exterior of the outer vessel. The support plug 10 may be configured to have a plurality of recesses each designed to receive a respective scaffold 10*a*.

Referring to FIG. 3, there is shown a second embodiment of the reactor 2. As with the first embodiment, the reactor 2 has an inner hollow cylinder 4 and an outer hollow cylinder 6, which together define an annular space 16 therebetween. However, in contrast to the reactor 2 shown in FIGS. 1 and 2, in the reactor shown in FIG. 3, the rotating cylinders 4,6 are mounted concentrically about the same rotational axis (i.e. not eccentrically). However, in order to produce a "pinch point" in the annular space 16 to generate hydrodynamic pressure gradients and shear stress, the wall of the inner cylinder 4 is provided with a series of protrusions 76, which extend transversely away from the plane of the cylinder wall 4 and into the annular space 16. The embodiment shown in FIG. 3 has two protrusions 78, although it will be appreciated that the number may be more depending on dimensions of the reactor 2. In use, upon relative rotational movement between the vessels 4,6 (i.e. either the inner and/or the outer cylinder rotates in either direction) the protrusions 76 move with respect to a corresponding point on the outer cylinder 6 wall, which causes the pinch points 78 to move around the annular space 16. Hence, the moving pinch points 78 cause the formation of pressure gradients, which in turn cause generate hydrodynamic pressure and shear stress in the space 16.

Referring to FIG. 4, there is shown a third embodiment of the reactor 2. This embodiment is similar to the second embodiment because the rotating cylinders 4,6 are mounted concentrically about the same rotational axis (i.e. not eccentrically). However, in order to produce a "pinch point" in the annular space 16 to generate hydrodynamic pressure gradients, the wall of the outer cylinder 6 is provided with a series of protrusions 76, which extend transversely away from the plane of the cylinder wall 6 and into the annular space 16. In use, upon relative rotational movement between the vessels 4,6 (i.e. either the inner and/or the outer cylinder rotates in either direction) the protrusions 76 move with respect to a corresponding point on the wall of the inner cylinder 4, which causes the pinch points 78 to move around the annular space 16. As with the previous embodiment, the moving pinch points 78 cause the formation of pressure gradients, which in turn cause generate hydrodynamic pressure and shear stress in the space 16.

A further embodiment of the reactor (which is not shown in the Figures) consists of the inner and outer cylinders 4,6 being mounted to rotate about different axes of rotation. In this embodiment, the distance between a point on the inner vessel 4 or on the inner surface of the outer vessel 6 and a radially opposing point on the other of the surfaces is non-uniform, during respective rotational movement between the two vessels 4,6. The effect of the non-uniform annular space is that the relative rotational movement of the vessels 4,6 produces the "pinch point" and therefore conditions favourable for hydrodynamic lubrication.

In a variation to the embodiments shown the support plug 10 may be designed such that it can be selectively biased radially inwardly (as well as removable in a radially outwards direction) towards the opposing vessel wall surface.

Figure 5:
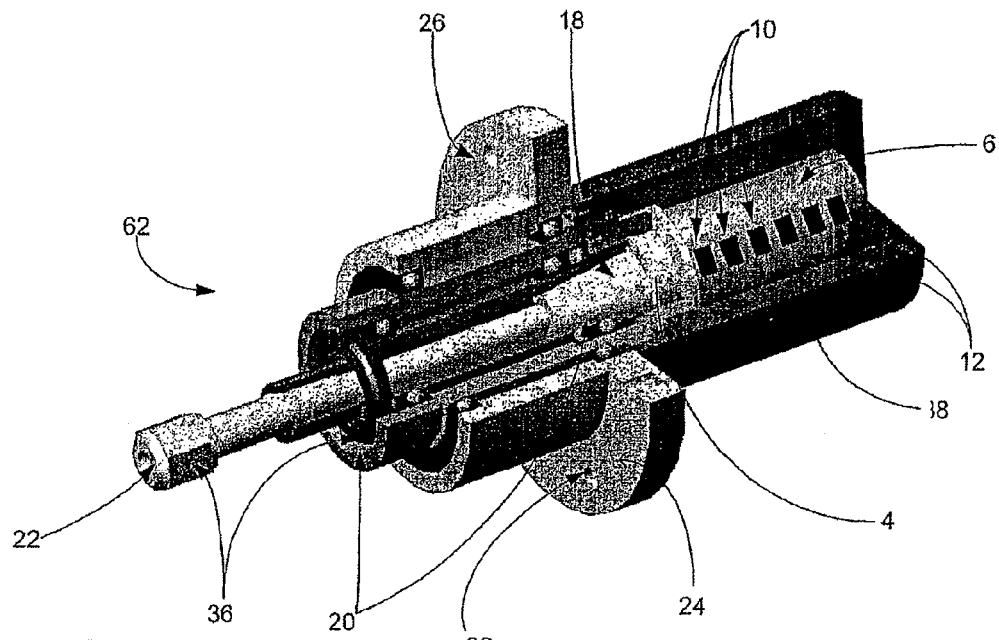
FIG. 5 shows a partial cross-sectional perspective view of the reactor shown in FIG. 1.

Referring to FIG. 5, there is shown the reactor 2 in greater detail with associated apparatus, thereby forming a reactor assembly 62. The outer cylinder 6 is covered with an end cap 38, which contains the reactant outlets 12 exiting each support plug 10 that is provided in each opening 8 in the wall of the outer cylinder 6. The inner cylinder 4 of the reactor 2 is mounted on a tapered shaft 18 that centres itself within the same bearing housing 20 that supports the outer cylinder 6, thereby enabling both cylinders 4, 6 to rotate freely and independently of one another about the same axis A-A. The shaft 18 is hollow having an inner channel 22 along which reactants such as air and other fluids (media) may be fed to the inner cylinder 4. The inner cylinder 4 is made of a porous or permeable material, which allows the inlet fluids to pass from the inner channel 22 and communicate with, and pressurise, the annular space 16 within the reactor 2.

As shown in FIG. 5, the end of the shaft 18 is fitted with a Luer lock attachment 36 to facilitate perfusion of fluid reactants, liquids, tissue culture medium etc into the channel 22, and through the reactor 2. A Luer lock 36 at the base of the outer cylinder 6 serves as a perfusion exit port for fluid exiting along conduits 12. The reactor 2 is provided with appropriate seals to prevent leakage.

Figure 6:
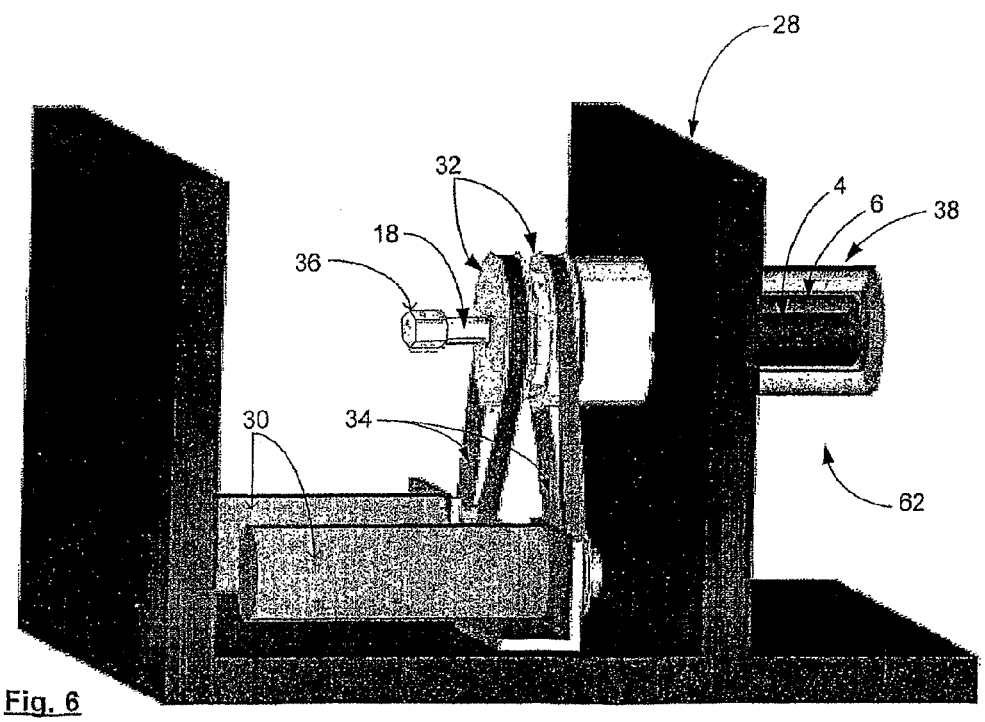
FIG. 6 shows a perspective view of the reactor shown in FIG. 5 assembled on a chassis with associated motors and a gearing mechanism.

As shown in FIG. 5, the reactor assembly 62 is provided with a supporting manifold 24, which has bolt holes 26 by which the entire assembly 62 may be attached to a support stand 28, as shown in FIG. 6. When in position on the support stand 28, rotation of the inner and outer cylinders 4, 6 of the reactor assembly 62 are independently powered by two servomotors 30 fixed to the base of the support stand 28. Each cylinder 4, 6 is connected to its corresponding servo motor 30 by means of a gearbox, pulley 32 and timing belt 34, as shown in FIG. 4. Therefore, by controlling the position, speed and direction of rotation of each cylinder 4, 6 by the servo motors 30, it is possible to control the distance between corresponding points on the opposing walls of the inner and outer cylinders 4,6, and hence the width of the annular space 16 therebetween. Hence, the speed of movement of the pinch point 78 in the annular space 16 is also controllable, and this will be determined by the specific biological or chemical reaction being carried out either in the annular space 16 or the recesses 8.

Figure 7:
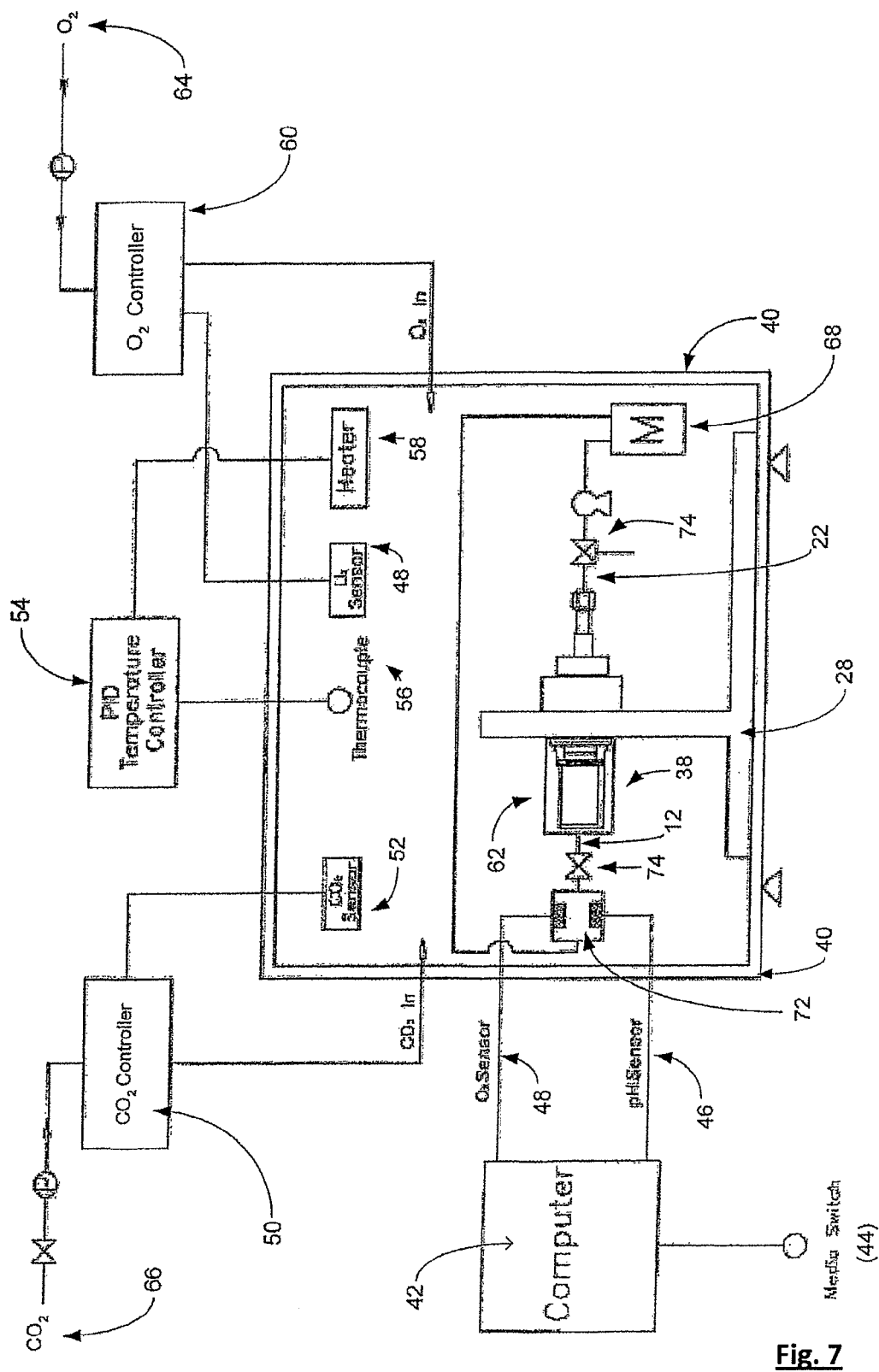
FIG. 7 shows a schematic view of the reactor contained within an environment chamber, and various control modules for operation of the reactor.

Referring to FIG. 7, there is shown a schematic layout showing the key peripheral components required to run and control the reactor 2 when in use. The support stand 28 supporting the reactor assembly 62 is placed inside an environment chamber 40, which is adapted to monitor and control various parameters of the environment for the reaction to occur, be it either biological or chemical. The environment chamber 40 is provided with a carbon dioxide sensor 52, a thermocouple 56, an oxygen sensor 48, and a heater 58. The temperature inside the environment chamber 40 is monitored by the thermocouple 56, and may be heated by the heater 58 under the control of a PID controller 54. The concentration of oxygen inside the chamber 40 is monitored by the oxygen sensor 48, and an oxygen supply 64 provides oxygen to the chamber 40 under the control of an oxygen controller 60. The concentration of carbon dioxide inside the chamber 40 is monitored by the sensor 52, and a carbon dioxide supply 66 provides carbon dioxide to the chamber 40 under the control of a carbon dioxide controller 50.

Fresh reactants, such as biological growth media, is provided to the reactor 2 by means of a media switch 44, which is fed into the reactor via a media supply 68 under the control of a computer 42. The fresh media supply 68 is connected to and passes through the channel 22 extending through the inside of the inner cylinder 4. Products of the reaction, and/or used media leaves the reactor 2 via outlet 14, which is connected to a flow through cell 72, which is itself connected to an oxygen sensor 48 and a pH sensor 46. The computer 42 monitors the pH and oxygen concentration of the media and ensures that the optimum pH and oxygen concentration of fresh media being fed into the reactor 2 are correct. Hence, the fresh media may be mixed with the media exiting the reactor 2 and adjusted accordingly so that the pH and all other parameters are optimal for the reaction to continue.

A reactor of the kind shown in FIGS. 1, 2, 5, 6 and 7 has been used to conduct preliminary tests in relation to the pressure variations at the pinch point. The reactor comprised two stainless steel co-axial and cylinders, the outer diameter of the inner being 30 mm and the inner diameter of the outer 32 mm. The degree of eccentricity of the outer cylinder was 1 mm, while the inner inner cylinder was covered in heat-shrink sleeving (FE27, Adtech Engineering) of nominal thickness 0.5 mm such that the two cylinders came into close contact without interfering with one another at the pinch point (to within machining and bearing tolerances) and approximately 2 mm apart at a point diametrically opposite.

The reactor was fitted with two pressure transmitters rated at 15 psi (1 bar or 100 kPa) (Sensortechnics, Puchheim, Germany), one of which was located at the pinch point, the other some distance away from the pinch point for reference purposes.

The following test runs were carried out at ambient room temperature and pressure:

The reactor was primed with pure glycerol (>99% pure, Sigma-Aldrich, Dorset, UK), the viscosity of which solution (0.5 Pa s at 25° C.) was measured independently in a constant stress/strain rheometer (StressTech, Reologica Instruments, Sweden).

Figure 8:
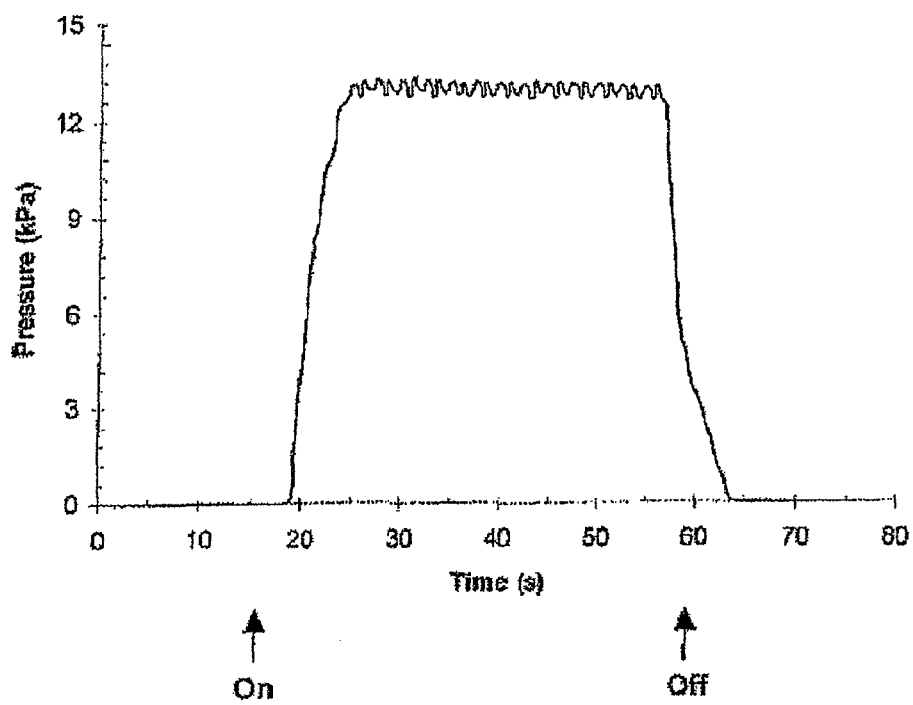
FIG. 8 is a graph illustrating the pressure difference between a pinch point in the reactor and reference point distal from the pinch point.

The inner cylinder was rotated at a constant speed and the absolute pressure recorded at the two locations. The pressure difference between these two locations increased immediately to a steady state pressure of 13.2 kPa at an angular speed of 4.0±0.1 radians per second (38±1 revolutions per minute) as shown in the graph of FIG. 8.

Figure 9:
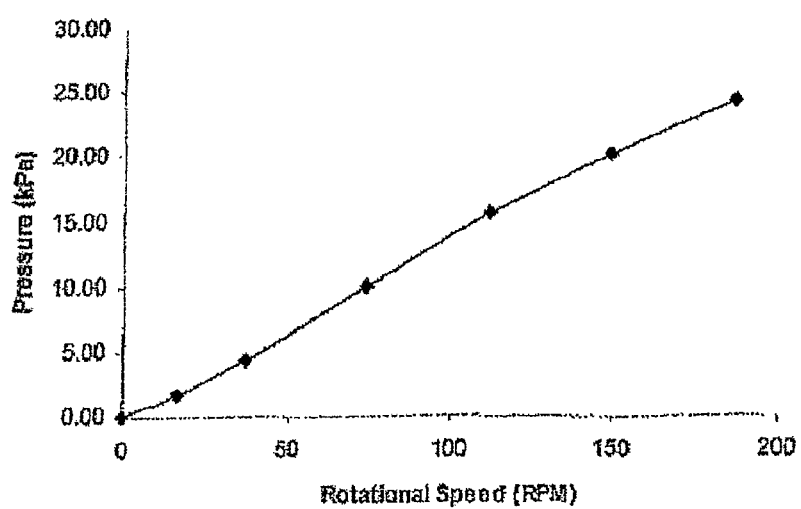
FIG. 9 is a graph that illustrates the relationship between the pressure difference and the relative rotational speed of the reactor vessels of FIG. 1.
Figure 10:
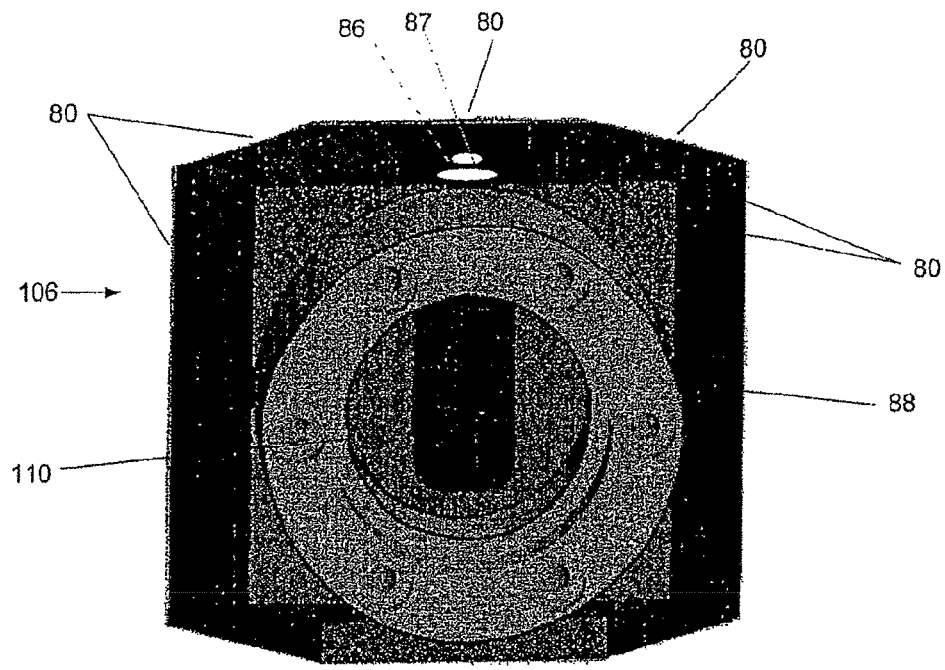
FIG. 10 is a front perspective view from above of a fourth embodiment of the reactor of the present invention, shown in simplified form.
Figure 11:
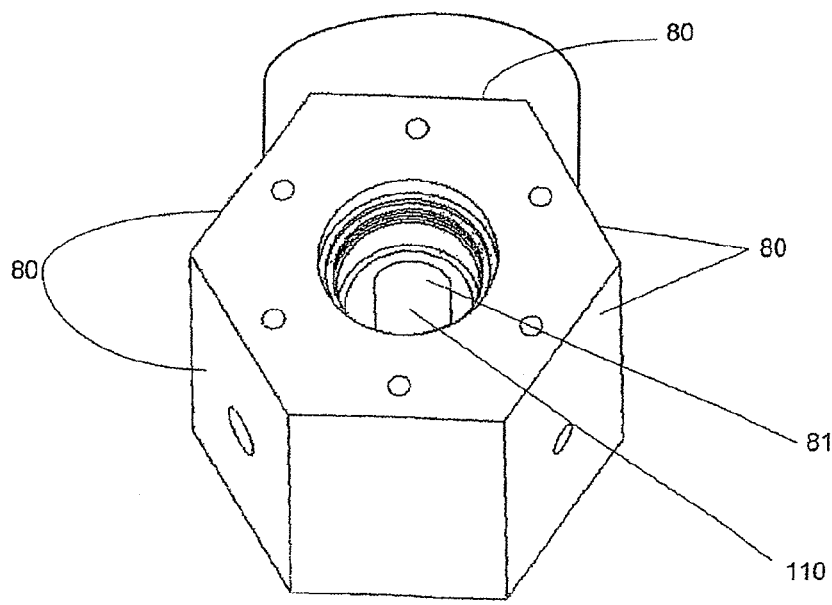
FIG. 11 is an underneath perspective view from below of the reactor of FIG. 10.
Figure 12:
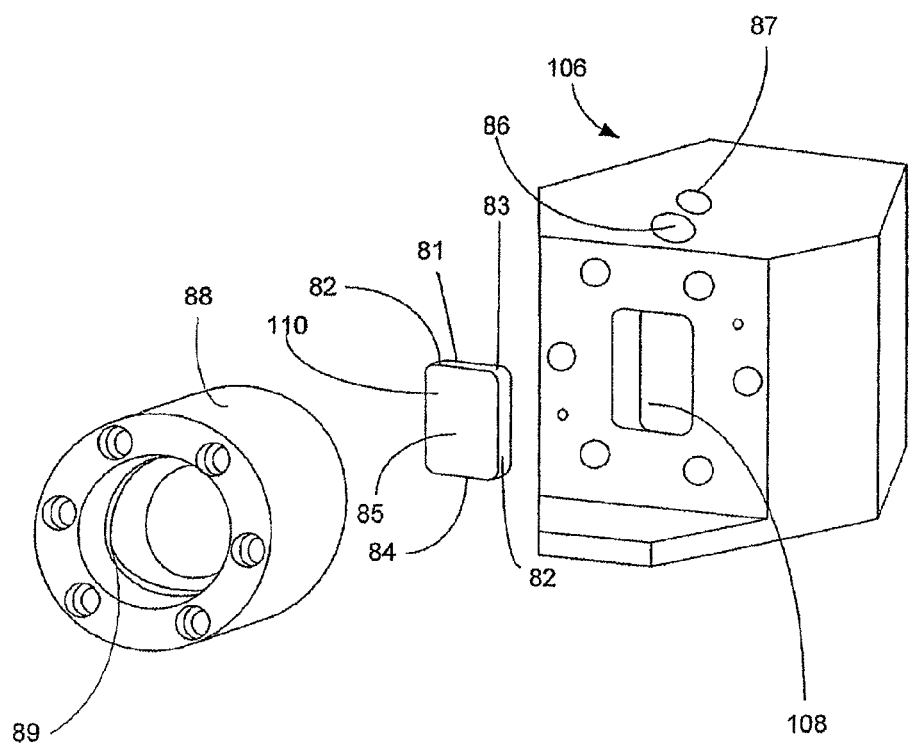
FIG. 12 is a partially exploded perspective view from one side of the reactor of FIG. 10.

In a separate experiment, the pressure was measured as a function of rotational speed and plotted in FIG. 9. The relationship was a linear one, the equation of the best-fit straight line having a regression coefficient, $R^2 > 0.99$.

It will be understood that numerous variations and modifications to this design of reactor are possible whilst still falling within the scope of the appended claims. For example, the exact size and shape of the reactor vessels can be varied provided that they are arranged in such a manner that their relative rotation creates the required hydrodynamic pressure and shear stress in the fluid when present in the annular space.

In an alternative embodiment of FIGS. 10 to 13 the reactor has an outer vessel with an exterior surface of generally hexagonal form thereby providing a plurality of flats 80 that facilitate the mounting of external components. Parts that are common to the reactors of FIGS. 1 to 5 are given the same reference numerals but increased by 100 and are not further described except in so far as they differ from their counterparts. The inner wall of the outer vessel 106 is cylindrical as before. The reactor is shown in a much simplified with many components removed for clarity. One of the walls is shown fitted with a removable support plug 110 that is received in a close-fitting sealing relationship within an opening 108 in the wall of the outer vessel 106. It is to be understood that other such support plugs 110 may be provided in the other flat walls 80 of the outer vessel. The support plug 110 is generally rectangular in profile when viewed from the rear and has an arcuate front surface 81 that, in use, faces the annular space 116 and conforms to the curvature of the inner surface of the outer vessel 106. The support plug 110 additionally has substantially parallel side walls 82, opposed parallel upper and lower walls 83, 84 and a rear wall 85. The side and upper and lower walls 82, 84, 84 are designed to be received by complementary walls defined by the opening 108, thereby enabling the support plug 110 to be slidable in the opening in a radial direction whilst always maintaining the seal. As in previous embodiments the front surface 81 defines one or more recesses for receipt of scaffolds (or other appropriate material to accommodate a biological or chemical reaction).

The top of the reactor is shown closed but for two ports. A larger port 86, disposed directly above the opening 108, penetrates the wall of the outer vessel 106 in a vertical direction and provides fluid communication with a passage defined in the upper wall 83 of the support plug 110. The other, smaller, port 87 disposed radially inboard of the larger port 86 provides fluid communication with the annular space 116. An annular collar 88 is bolted to the flat wall 80 around the support plug 10 and is designed to receive a hydraulic actuator (not shown) that is fixed against an internal step 89 in the collar. In use, the actuator is operable to apply a biasing force to the rear wall 85 of the support plug 110 thereby biasing it towards the inner vessel 104.

Fluid from a media reservoir is delivered into the reactor via port 87 (which also allows air to bleed out). During operation of the reactor in the manner described above the fluid passes through the scaffold and membrane (not shown in FIGS. 10 to 12) to passages provided in the support plug and out through the port 86. The support plug 110 can be optionally loaded by applying a force via the actuator to bias it radially inwardly and counteract the force applied by virtue of the relative rotation of the vessels, thereby providing favourable conditions for the reaction. The pressures developed under these loading conditions can be relatively high since the surface of the support effectively acts as a bearing surface that bears upon the rotating surface of the inner vessel thereby reducing the thickness of the film between them.

Figure 13:
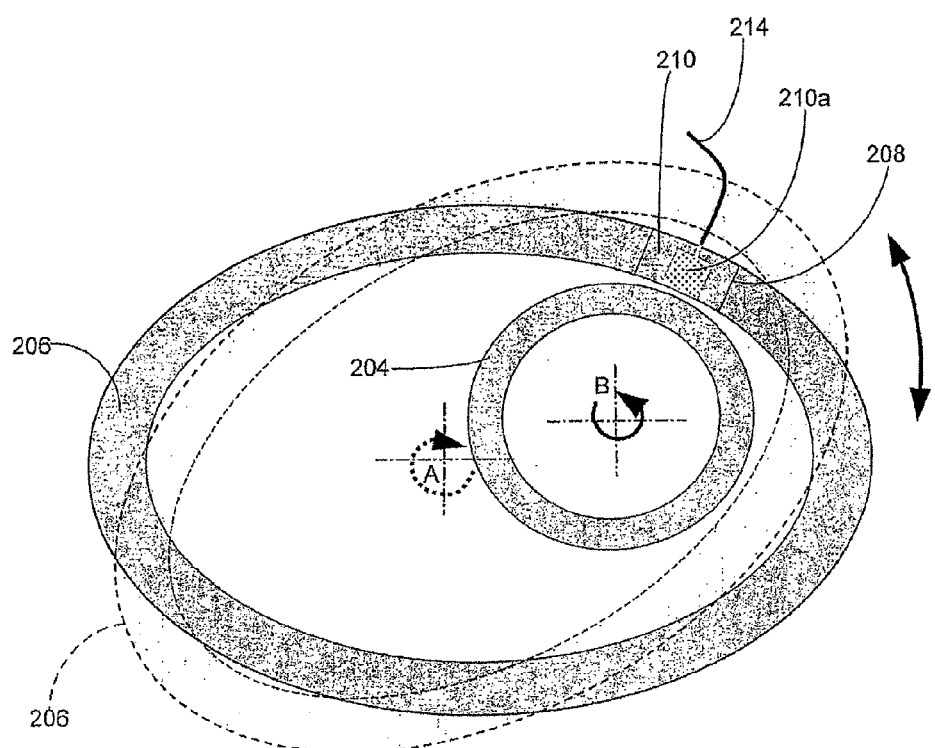
FIG. 13 is a schematic representation in plan of a fifth embodiment of the reactor of the present invention.

In the embodiment shown in FIG. 13, the outer vessel 206 is defined by an elliptical wall that is driven to oscillate about an axis A between a first position shown in solid line and a second position shown in dotted line. As in previous embodiments the wall has an opening 208 that is closed by a removable support plug 210 designed to receive a scaffold 210a or equivalent. The inner vessel in this embodiment is cylindrical and rotates about its central axis B. The relative rotation of the vessels creates the desired hydrodynamic conditions by repeatedly "opening" and "closing" the pinch point (represented in the figure at X). The movement of the outer vessel may be such that there is inference is made between the inner and outer vessels 204, 206 thereby applying a load to the support plug 210 and scaffold 210a. The free rotation of the inner vessel 204 maintains hydrodynamic lubrication thereby preventing direct contact between the vessels. The torque applied to drive the outer vessel in oscillation is selected such that the pressure is less than that generated by the hydrodynamic lubrication.

Example 2

Use of the Reactor to Control a Biological Reaction

It will be appreciated that the reactor 2 could be used for a wide range of biological reactions. By way of example, the following example describes using the reactor 2 for culturing mammalian cells and tissues in vitro, e.g., bone and/or cartilage tissue.

Referring to FIG. 5, the bioreactor assembly 62 is first assembled in a laminar flow hood (or equivalent) where biomaterial plugs or scaffolds 10 are inserted into each of the recesses 8 in the wall of the outer cylinder 6. The recesses 8 are then covered with a permeable support membrane 11, as shown in FIG. 1. Media perfusion lines and a media reservoir 68 are then connected to the bioreactor 2 in a clean room environment. Sterile tubing is attached to the perfusion exit port 14 and to the return line of the media reservoir using Luer connections 36. Bone and/or cartilage cells (chondrocytes) are then introduced by bolus injection into the bioreactor 2 via the inlet perfusion line 22 using a syringe with the Luer lock 36, which is connected to the inlet line in the laminar flow hood. The cells accumulate in and populate the scaffolds 10.

The bioreactor assembly 62 shown in FIG. 5 is then attached by the manifold 24 to the support 28 as shown in FIG. 6, which is then transferred to an environment chamber 40 as shown in FIG. 7. The media reservoir 68 is filled with culture medium, capped, and vented through a 0.2 μm filter to facilitate sterile gas exchange to the medium. The system is then primed with cell-free culture media by means of a low-flow pump (IsmaTec, Switzerland).

Referring to FIG. 7 suitable environmental conditions are then set up in the chamber 40 so that the reaction may be carried out. The chamber 40 is maintained at 37° C. and 5% $CO_2$ concentration with appropriate humidity. Carbon dioxide is regulated using the Portomatic controller 50 (Thermo-Forma, UK), and temperature is regulated with the PID temperature controller 54 (Carel, Italy).

For cartilage tissue engineering applications, the environment chamber 40 is regulated for hypoxia (low oxygen concentration). Since native cartilage experiences a range of oxygen tensions, this is likely to vary between 1 and 15% (Percent Saturation). Oxygen concentration regulation in the chamber 40 is achieved using the ProOx110 Oxygen controller 60 (Biospherix, Redfield, N.Y.). The flow through cell 72 has been designed to accommodate optical sensing foils for oxygen concentration and pH immediately downstream of the bioreactor 2. Online monitoring takes place via pH 46 and oxygen 48 controllers (PreSens GmbH) linked to the computer 42. This information is used to actuate solenoid valves 74 to switch to alternative media supply at the correct time or to control the pump for media perfusion.

Further bone and/or cartilage cells are introduced into the inlet line 22 and allowed to perfuse through the interstitial spaces of the scaffolds 10 thereby forming a so-called tissue construct, the surfaces of which are typically modified to promote cell adhesion. Once the cells have attached and proliferated within the constructs 10, perfusion is applied intermittently as and when nutrients are required, this being determined from pH and oxygen consumption data.

The inner and outer cylinders 4, 6 of the reactor 2 are rotated as and when appropriate, also in a prescribed manner, under the power of the two servo motors 30. As shown in FIG. 2, the eccentricity of the rotation of the two cylinders 4, 6 causes the shape of the annular space 16 to be varied which in turn imparts radial loading on the constructs 10 with a magnitude and frequency that is governed by the speed of rotation and degree of eccentricity of the cylinders 4, 6. The radial loading causes the pinch point 78 to form at the position of the recesses 8. Hence, the pressure gradients that develop by virtue of the relative motion of the two cylinders 4, 6 gives rise to periodic deformation and media flow through the constructs 10. In use, when a tissue culture is grown in the reactor 2, the tissue scaffold 10 will adopt the shape of the opening 8, which in its simplest form will be a plug or cylinder with opposing faces exposed to the annulus 16 on the one hand, and ports on the outer surface of the cylinder 6 on the other.

The degree of hydrodynamic pressure loading and fluid shear stress applied to the constructs 10 may be adjusted accordingly throughout the period of culture via control of the speed and direction of rotation of the cylinders 4, 6, as can media perfusion, media exchange and oxygen tension. The result of the culture in the bioreactor 2 is that the in vitro conditions provided in the annular space 16 are much more realistic and comparable to the growth environment in vivo for cartilage. Hence, cartilage produced by growing in the bioreactor 2 according to the invention are much improved to that which is grown using current in vitro culture apparatus and techniques.

Once the culture is completed, and sufficient cells have populated the constructs 10, the reactor 2 is then stopped and removed from the environment chamber 40. In a clean room environment, the reactor is dismantled such that the constructs 10 can be removed and then used as implants as required.

Example 3

Use of the Reactor to Control a Chemical Reaction

The reactor 2 may also be used to carry out chemical reactions, for example, the polymerisation and subsequent processing (extrusion) of a thermoplastic polyurethane following the mixing of prepolymer with a suitable chain extender. The polyurethane prepolymers are prepared by feeding polyol with polyisocyanate in the annular space 16, allowing them to mix in the space 16 at elevated temperature (i.e. 40° C.) and stopping the reaction before the polymerisation is complete. Thereafter, the prepolymer and a suitable chain extender (e.g. diol) are fed into the space 16, and then combined in the reactor 2 and extruded under pressure through a die. The pressure in the space 16 causes the polymer product to be extruded through the recesses 8.

Examples of suitable diols include 1,6-hexane diol, 2-ethyl-1,3-hexanediol (EHD), and 1,4-Butanediol. The preferred low molecular weight glycol is 1,4-Butanediol. The polyisocyanates may be selected from a wide range of aliphatic, cycloaliphatic and aromatic polyisocyanates. Examples of suitable aromatic polyisocyanates are methyl-diisocyanate (MDI) and toluene diisocyanate (TDI). The polyol may be either a polyester or a polyether. An example of a polyether polyol is polytetramethylene glycol. The product of the reaction is therefore a poly(ether)urethane urea.

As mentioned above, once the polymerisation is completed, the polymer product may be removed from the reactor either by extrusion while the reactor 2 is still being actuated, or by stopping the reactor 2 and then removing the polymer from the annular space.

SUMMARY AND CONCLUSIONS

The inventors carried out extensive investigations in to the fluid flow characteristics of the reactor 2 according to the invention, and have obtained empirical evidence that the eccentricities of the cylinders significantly enhance the generation of Taylor vortex flow regimes and of hydrodynamic pressure and of shear stresses within the annular space 16 in the reactor 2. Such hydrodynamic pressure and shear stress can be put to use in either a chemical or biological reaction.

For example, the inventors have demonstrated that the reactor 2 can be effectively used to carry out polyurethane synthesis as described in Example 3.

In addition, the inventors have demonstrated that the reactor 2 can be effectively used to support the growth and differentiation of cells in vitro, with or without scaffold 10 support, into viable osteochondral tissue constructs 10, as described in Example 2. They have demonstrated that Taylor vortex flow regimes in the reactor 2 significantly enhance axial oxygen transport therein, thereby overcoming the limitations in oxygen transport that are inherent in laminar Couette flows obtained by using prior art reactors. Hence, the use of the reactor 2 according to the invention, exhibits a marked improvement in structure and function over existing Tissue Engineering products owing to the well-defined physico-chemical environment that exists within the bioreactor 2. Hence, the reactor 2 achieves physiological loading conditions in a manner far more representative of diarthroid synovial joints than in existing RWV reactors.

The reactor 2 differs from traditional RWV reactors in several respects. It exploits the relative motion of the inner and outer cylinders 4, 6 to generate hydrodynamic pressure within the annular space 16. These 'self-generated' pressure gradients give rise to deformation of the fluid in the annular space 16, and flow through the construct 10 itself (interstitial flow), and may also be used to drive fluid through the reactor 2 and any external perfusion circuit to which it may be attached. The consequences of this are profound and give rise to a number of unique features. The inventors believe that such fluid flows may be exploited to improve the uniformity of initial seeding with cells, and subsequently, to improve the functional properties of three-dimensional cell-seeded scaffolds 10 through improvements in mass transport i.e. not just in the bioreactor, but within the construct 10 itself. Hence, the result is an improvement in the uniformity of initial cell seeding and improved growth of cells on the scaffold 10 structures.

Hence, the inventors believe that the reactor 2 can be used to promote the formation and maturation of load-bearing cartilaginous or fibro-cartilaginous tissue in vitro through the application of cyclic hydrodynamic and rheological loading to the porous biomaterial scaffolds 10 that have been seeded with cells (e.g. autologous chondrocytes, mesynchymal stem cells, etc.). The inventors have surprisingly found that the reactor 2 improves the uniformity of seeding and the functional properties of three-dimensional cell-seeded scaffolds 10 by culturing them under hydrodynamic conditions that simulate loading conditions found in vivo in normal physiological conditions, compared to hydrostatic pressure and deformation alone found in prior art reactors. The reactor 2 allows the preconditioning of the cartilage or other constructs by means of steady or cyclic, intermittent (variable duty cycle) motion of the inner and outer cylinders 4,6 about their respective axes of rotation.

The reactor further provides a means by which the tissue constructs 10 can be subjected to fluid shear forces or stresses across the surface of the construct 10 by virtue of the viscous properties of the culture medium and the flow patterns within the annular space 16, as prescribed by the axial transport (i.e. perfusion) of the fluid and/or the relative motion and separation of opposing surfaces of the cylinders 4, 6.

Furthermore, the reactor 2 provides a means by which the tissue constructs 10 are subjected to fluid shear forces generated by the convective transport of media through the interstices of the scaffold constructs 10. The recesses 8 provide a suitable housing, which may be occupied by one or more constructs 10, whereby opposite aspects of the constructs 10 are exposed to physical and biochemical factors that promote cartilage formation on the one hand, and bone formation on the other. The microporous interface(s) or membranes 11 provide a surface through which dissolved gases, nutrients, waste products, solutes, or other product may be transported to and from the constructs 10 by diffusion and convection, alone or in combination.

The environment chamber 40 provides a way in which the temperature, oxygen/carbon dioxide tensions, solute concentrations etc., may be carefully monitored and controlled. It is also possible to monitor such environmental variables as may be deemed necessary to ascertain the metabolic status and permeability of the constructs 10 by means of appropriate transducers, instrumentation etc., in real time through the use of sampling ports, in line probes etc. Furthermore, the reactor assembly comprises communicating channels as necessary to allow for the steam sterilization of all the internal surfaces. The reactor 2 incorporate bearing(s) 20 that do not compromise sterility or damage, or contaminate the product through the generation of excessive heat and/or wear particles, or to ensure their removal from the culture medium with the aid of filters.

Further advantages of the reactor reside in the effective manner in which hydrodynamic pressure and shear stresses may be produced in the annular space 16 between the inner and outer cylinders 4, 6. Hence, the reactor 2 according to the invention is able to automatically generate its on pressurization in the annular space 16, thereby obviating the requirement for an external pressurization source.

The reactor 2 according to the invention provides a means by which the tissue constructs 10 are subjected to controlled and variable interstitial flow by virtue of the hydrodynamic pressures developed in the culture medium. In addition, the reactor provides a way by which the tissue constructs 10 are subjected to hydrodynamic or hydrostatic pressure (at times when the vessels 4,6 of the reactor 2 are not rotating relative to each other) within the internal annular space 16 of the bioreactor 2. It also provides a means by which the tissue constructs 10 are subjected to fluid shear forces across the surface of the construct 10 by virtue of the viscous properties of the culture medium and the flow of culture medium in the axial direction by means of perfusion. The microporous membranes 11 or filters facilitate gas-exchange, diffusion of solutes etc., across the air/liquid and liquid/tissue interface(s).

It is to be appreciated that the viscosity of the fluid in the reactor has an impact on the hydrodynamic pressure and shear forces and can be altered (by the introduction of suitable polymers or the like) to achieve the desired conditions.

The reactor 2 promotes very efficient cell seeding under dynamic conditions as detailed above, and facilitates the delivery of growth factors, and chemotactic factors, etc., to the constructs. In use, it is possible to establish differential concentration gradients of such growth factors, chemotactic factors, etc., through the constructs under the hydrodynamic conditions as detailed above. The reactor 2 also allows the harvesting of any product from the culture medium that may be produced by the cells under the specific hydrodynamic conditions as detailed above. Furthermore, it is possible to expose the construct 10 to different media on either aspect (side) of the constructs 10 under the hydrodynamic conditions. Finally, the flow patterns, shear stresses, mass transport in the reactor (the annular space 16 and the recesses 8) may be reproduced on any practicable length scale (aspect ratio, radius ratio, etc.).

The invention claimed is:

1. A biological or chemical reactor comprising an inner vessel disposed within an outer vessel, which vessels define a substantially annular space therebetween in which fluid is to be contained, which fluid comprises reactants of a biological or chemical reaction, wherein relative rotational movement between the vessels produces a pinch point and generates hydrodynamic pressure and shear stress in the fluid within the annular space; and
a reaction containment feature provided on or in a wall of the inner and/or outer vessel, wherein the reaction containment feature is positioned at or adjacent to the pinch point.

2. A reactor according to claim 1, wherein, the outer vessel is substantially hollow and the inner vessel is disposed therein.

3. A reactor according to claim 1, wherein the inner vessel is substantially hollow.

4. A reactor according to claim 1, wherein the outer vessel comprises a first wall defining an inner surface, and the inner vessel comprises a second wall defining an outer surface.

5. A reactor according to claim 4, wherein the inner surface of the outer vessel opposes the outer surface of the inner vessel thereby defining the annular space therebetween.

6. A reactor according to claim 5, wherein said surfaces are generally cylindrical.

7. A reactor according to claim 4, wherein the outer surface of the inner vessel and/or the inner surface of the outer vessel is non-uniform or substantially uneven.

8. A reactor according to claim 7, wherein the outer surface of the inner vessel and/or the inner surface of the outer vessel has at least one raised and/or lowered portion.

9. A reactor according to claim 8, wherein there is a plurality of raised and/or lowered portions disposed at various positions around the vessel.

10. A reactor according to claim 8, wherein the raised portion comprises a protrusion that projects away from the surface of the vessel.

11. A reactor according to claim 8, wherein the lowered portion comprises an indentation or recess in the surface.

12. A reactor according to claim 5, wherein the radial distance between the inner surface of the outer vessel and the outer surface of the inner vessel is not constant about the circumference of the annular space.

13. A reactor according to claim 12, wherein the distance between a point on the outer surface of the inner vessel or on the inner surface of the outer vessel and a radially opposing point on the other of said surfaces varies upon relative rotational movement between the vessels.

14. A reactor according to claim 1, wherein the inner vessel is rotatable about a first axis and the outer vessel is rotatable about a second axis.

15. A reactor according to claim 14, wherein the inner vessel and the outer vessel are rotatable about respective first and second axes independently of each other.

16. A reactor according to claim 14, wherein the first and second axes are coincident.

17. A reactor according to claim 14, wherein the first and second axes are offset.

18. A reactor according to claim 1, wherein the vessels are eccentrically mounted.

19. A reactor according to claim 1, wherein the inner and outer vessels are rotatable at different speeds.

20. A reactor according to claim 1, wherein the inner and outer vessels are rotatable in the same or opposite directions.

21. A reactor according to claim 1, wherein one of the vessels is rotatable about a first axis and the other vessel is fixed against rotation.

22. A reactor according to claim 21, wherein the fixed vessel has a second central axis that is coincident with, or offset from, said first axis.

23. A reactor according to claim 1, wherein the relative rotational movement is limited to less than 360 degrees.

24. A reactor according to claim 1, wherein the relative rotational movement is limited to less than 90 degrees.

25. A reactor according to claim 1, further comprising a drive that is operable to control the direction and/or speed of and/or torque applied to the, or each, vessel.

26. A reactor according to claim 1 comprising a fluid feed for feeding fluid to the annular space.

27. A reactor according to claim 26, where the fluid feed comprises a conduit through which the fluid is fed.

28. A reactor according to claim 27, wherein the reactor comprises at least one drive shaft for imparting said relative rotation and the conduit is associated with, or extends through, the drive shaft.

29. A reactor according to claim 26, wherein the fluid feed comprises at least one inlet with a valves or connectors.

30. A reactor according to claim 29, wherein the valve or connector is a compression fitting.

31. A reactor according to claim 26, wherein the inner vessel is adapted to allow the fluid to pass therethrough.

32. A reactor according to claim 31, wherein, in use, the fluid passes from the conduit and into the annular space.

33. A reactor according to claim 31, wherein any part of the wall of the inner vessel is substantially permeable or porous.

34. A reactor according to claim 1, wherein the containment feature is positioned to be in fluid communication with the annular space such that the fluid, and hence, reactants may flow therebetween.

35. A reactor according to claim 1, wherein the containment feature is in fluid communication with the exterior of the reactor such that reactants may flow therebetween and away from the annular space.

36. A reactor according to claim 1, wherein the reaction containment feature comprises at least one recess, channel or fenestration provided in, or extending through, the wall of the inner and/or outer vessel.

37. A reactor according to claim 36, wherein a reaction containment feature is provided in the, or each, moving vessel.

38. A reactor according to claim 36, wherein said at least one recess, channel or fenestration is provided in the outer wall of the inner vessel.

39. A reactor according to claim 36, wherein said at least one recess, channel or fenestration is provided in the inner wall of the outer vessel.

40. A reactor according to claim 1, wherein the containment feature comprises a plurality of recesses, channels or fenestrations that are spaced apart along the axis of the vessel.

41. A reactor according to claim 40, wherein the reaction containment feature comprises a plurality of spaced apart recesses, channels or fenestrations which are aligned substantially along the longitudinal axis of the vessel.

42. A reactor according to claim 1, wherein there is provided a support in the reaction containment feature and in which the reaction may be carried out.

43. A reactor according to claim 42, wherein the support is adapted to allow fluid to flow therethrough.

44. A reactor according to claim 43, wherein the support defines passages through which the fluid may flow.

45. A reactor according to claim 42, wherein the support supports at least one scaffold structure.

46. A reactor according to claim 42, wherein the support is mounted such that it is substantially in the same plane as the surface of the wall in which is it is fitted.

47. A reactor according to claim 42, wherein the support is not flush with surface and has a contoured surface that faces the annular space.

48. A reactor according claim 42, wherein the support is placed under load within the containment feature in order to contribute to, and withstand, the build up of hydrodynamic pressure within the annular space upon relative rotational movement between the vessels.

49. A reactor according to claim 48, further comprising an actuator for applying said load to said support.

50. A reactor according to claim 49, wherein the actuator is a pneumatic or hydraulic ram.

51. A reactor according to claim 49, wherein the actuator is a biasing member.

52. A reactor according to claim 51, wherein the biasing member is a spring.

53. A reactor according to claim 42, wherein the support is removable from the containment feature.

54. A reactor according to claim 53, wherein the support is adapted to be moved in a direction, which is substantially normal (perpendicular) to the surface in which the containment feature is provided.

55. A reactor according to claim 53, where the support is adapted to tilt as it is moved in or out of the containment feature.

56. A reactor according to claim 42, further comprising a porous membrane disposed between the reaction containment feature and the annular space and/or a fluid path leading to the outside, which membrane is adapted to control the flow of fluid to and from the reaction containment feature.

57. A reactor according to claim 56, wherein the membrane extends across at least part of the containment feature and the support means.

58. A reactor according to claim 1, further comprising a fluid outlet adapted to regulate the removal of fluid from the annular space.

59. A reactor according to claim 58, wherein the fluid outlet is in fluid communication with the annular space and the containment feature.

60. A reactor according to claim 58, wherein the reactor comprises a fluid re-circulation member adapted to re-circulate fluid exiting the annular space via the outlet, and back into the annular space.

61. A reactor according claim 60, further comprising a fluid mixer adapted to mix the fluid in the outlet with fluid from a fluid feed.

62. A reactor according to claim 1, further comprising a securement device adapted to secure the reactor in any spatial orientation.

63. A reactor according to claim 62, wherein the securement device comprises a manifold, which is adapted to be secured to a support stand.

64. A reactor according to claim 1, wherein the reactor is adapted to rotate the axis of rotation of the vessels, in order to affect, counteract, alter or reverse the effects of gravity.

65. A reactor according to claim 1, mounted about a rotational axis, which axis is independent of the rotational axis or axes of the inner and outer vessels.

66. A reactor according to claim 1, further comprising at least one monitoring and control device for controlling reaction variables within the reactor.

67. A biological or chemical reactor comprising an inner vessel disposed within an outer vessel, which vessels define a substantially annular space therebetween in which fluid is to be contained, the outer vessel having a first wall defining an inner surface and the inner vessel having a second wall defining an outer surface, at least one reaction containment feature is provided on or in a wall of the inner and/or outer vessel, the containment feature being positioned to be in fluid communication with the annular space such that the fluid, and hence, reactants may flow therebetween, the reaction containment feature comprising at least one support that is received in a recess, channel or fenestration in the wall, the vessels being rotatable relative to one another such that the distance between a point on the outer surface of the inner vessel or on the inner surface of the outer vessel and a radially opposing point on the other of said surfaces varies so as to generate hydrodynamic pressure and shear stress in the fluid disposed in the annular space.

68. The reactor according to claim 1, wherein the relative rotation of the vessels causes the distance between respective surfaces of the vessels to vary with respect to time, in a cyclic or reciprocating manner.

69. The reactor according to claim 1, wherein the distance between opposing points on the vessels varies with respect to time.

70. The reactor according to claim 1, wherein the variation in distance with respect to time is linear, non-linear, stepped or sinusoidal.

71. The reactor according to claim 1, wherein the speed and direction of rotation is varied between vessels.

72. The reactor according to claim 1, wherein the speed and direction of rotation is varied with respect to time.

73. The reactor according to claim 19, wherein the relative motion/movement of the first and second axes causes the distance between respective surfaces of the vessels to vary with respect to time, in a cyclic or reciprocating manner.

74. The reactor according to claim 23, wherein the distance between opposing points on the vessels varies with respect to time.

75. The reactor according to claim 24, wherein the variation in distance with respect to time is linear, non-linear, stepped or sinusoidal.

76. The reactor according to claim 19, wherein the speed and direction of the relative motion (of the axes) is varied between vessels.

* * * * *

UNITED STATES PATENT AND TRADEMARK OFFICE
CERTIFICATE OF CORRECTION

PATENT NO. : 8,342,735 B2  
APPLICATION NO. : 12/088892  
DATED : January 1, 2013  
INVENTOR(S) : Black et al.

Page 1 of 1

It is certified that error appears in the above-identified patent and that said Letters Patent is hereby corrected as shown below:

In the Claims

<u>Column 28,</u>
Line 10, "claim 58" should read --claim 59--.

Signed and Sealed this
Twenty-first Day of May, 2013

Teresa Stanek Rea
*Acting Director of the United States Patent and Trademark Office*